(12) United States Patent
Adams et al.

(10) Patent No.: US 6,300,485 B1
(45) Date of Patent: Oct. 9, 2001

(54) MYOSIN IXA AND CYCLIC NUCLEOTIDE GATED CHANNEL-15 (CNGC-15) POLYNUCLEOTIDES, POLYPEPTIDES, COMPOSITIONS, METHODS, AND USES THEREOF

(75) Inventors: Arwen E. Adams, Oakland; Choi Ying Chiu, Castro Valley; David Duhl, Oakland; Susan W. Gorman, Santa Monica; Song Leng, Castro Valley, all of CA (US); Val Sheffield, Iowa City, IA (US); Juliet Welch, Kensington, CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 09/172,422

(22) Filed: Oct. 14, 1998

Related U.S. Application Data

(60) Provisional application No. 60/062,858, filed on Oct. 15, 1997, provisional application No. 60/062,241, filed on Oct. 17, 1997, and provisional application No. 60/068,953, filed on Dec. 30, 1997.

(51) Int. Cl.$^7$ .................................................. C07H 21/02
(52) U.S. Cl. .................... 536/23.1; 536/23.4; 536/24.31; 536/24.1
(58) Field of Search ................................. 536/23.1, 23.4, 536/24.31, 24.1; 530/350; 435/252.3

(56) References Cited

PUBLICATIONS

Geysen et al Cognitive features of continuous antigenc determinants. (J. of Molecular Recognition, vol. 1, pp. 32–40, 1988).*
EST Accession No. AA279085 (Aug. 15, 1997).*
Reizes et al. Domain structure of a mammalian myosin 1beta. (Proc. Natl. Acad. Sci. USA, vol. 91, pp. 6349–6353, 1994).*
EST Accession No. AA494302, made publicly available Aug. 20, 1997.*
EST Accession No. AA398548, made publlicly available Apr. 28, 1997.*
EST Accession No. AA287851, made publicly available Apr. 12, 1997.*
Emest Database Entry, Accession No. AA279085, Apr. 3, 1997.
Emest Database Entry, Accession No. AA287851, Apr. 12, 1997.
Emest Database Entry, Accession No. AA398548, Apr. 28, 1997.
Emest Database Entry, Accession No. AA403319, May 1, 1997.
Emest Database Entry, Accession No. AA425434, May 24, 1997.

Bement et al., "Identification and Overlapping Expression of Multiple Unconventional Myosin Genes in Vertebrate Cell Types," *Proc. Natl. Acad. Sci. USA* 91:6549–6553, 1994.
Post, et al., "Human Myosin IX—A Novel Unconventional Myosin with a Chimaerin–Like RHO/RAC Gap Homology Domain in its Tail" *Molecular Biology of the Cell*, (1995) vol. 6, No. suppl., pp. 144A.
GenBank Report, Accession No. N727770, Hillier, et al., "The WashU–Merck EST Project" Unpublished, Washington University School of Medicine.
Weil, et al., "Human Myosin VIIA Responsible for the Usher 1B Syndrome: A Predicted Membrane–Associated Motor Protein Expressed in Developing Sensory Epithelia" *Proc. Natl. Acad. Sci. USA*, (Apr. 1996) vol. 93, pp. 3232–3237.
Hasson, et al., "Vertebrate Unconventional Myosins" *The Journal of Biological Chemistry*, (1996) vol. 271, No. 28, Issue of Jul. 12, pp. 16431–16434.
Wells, et al., "Myogenic Cells Express Multiple Myosin Isoforms" *Journal of Muscle Research and Cell Mobility*, (1997) vol. 18, pp. 501–515.
Santoro, et al. "Identification of a Gene Encoding a Hyperpolarization–Activated Pacemaker Channel of Brain" *Cell*, (May 29, 1998) vol. 93, pp. 717–729.
John R. Glenney, Jr. and Klaus Weber, "Calmodulin–binding Proteins of the Microfilaments Present in Isolated Brush borders and Microvilli of Intestinal Epithelial Cells" The Journal of Biological Chemistry, vol. 255, No. 22, Nov. 25, 1980, pp. 10551–10554.

(List continued on next page.)

*Primary Examiner*—John S. Brusca
*Assistant Examiner*—Young Kim
(74) *Attorney, Agent, or Firm*—Jane E. R. Potter; Kimberlin L. Morley; Robert P. Blackburn

(57) ABSTRACT

The present invention discloses the amino acid and nucleic acid sequences of a new CNGC and Myosin that map to the region of the human chromosome associated with Bardet-Biedl Syndrome. Cyclic nucleotide gated channels (CNGCs) comprise a family of multimeric protein ion channels that open in response to the binding of a cyclic nucleotide to an intracellular domain. The two new proteins, CNGC-15 and Myosin IXa, are useful in the study, diagnosis and treatment of Bardet-Biedl Syndrome and Usher Syndrome. Other indications that can be treated by CNGC-15 and/or Myosin IXa polypeptides, or agonists or antagonists include hearing loss, retinis pigmentosa, obesity, hypogonadism, sterility, polydactyly, brachydactyly, syndactyly, mental retardation, renal abnormalities, hypertension, diabetes and cardiovascular abnormalities.

Compositions and methods for expressing cyclic nucleotide gated channel-15 (CNGC-15) and Myosin IXa are provided. The compositions comprise CNGC-15 and Myosin IXa polypeptides and derivatives thereof, nucleotide sequences, expression cassettes, transformed cells and antibodies to these polypeptides. Methods for the expression and detection of CNGC-15 and Myosin IXa nucleotides and polypeptides and compositions for the treatment of these conditions are provided.

9 Claims, 7 Drawing Sheets

OTHER PUBLICATIONS

Kathleen Collins, et al., "Calmodulin Dissociation Regulates Brush Border Myosin I (110)–kD–Calmodulin) Mechanochemical Activity In Vitro" Journal of Cell Biology, vol. 110, Apr. 1990, pp. 1137–1147.

Anne J. Ridley and Alan Hall, "The Small GTP–Binding Protein rho Regulates the Assembly of Focal Adhesions and Actin Stress Fibers in Response to Growth Factors" Cell, vol. 70, Aug. 7, 1992, pp. 389–399.

Ridley, et al., "The Small GTP–Binding Protein rac Regulates Growth Factor–Induced Membrane Ruffling" Cell, vol. 70, Aug. 7, 1992, pp. 401–410.

Ruppert, et al., "Identification, characterization and Cloning of myr 1, a Mammalian Myosin–I" Journal of Cell Biology, vol. 120, No. 6, Mar. 1993, pp. 1393–1403.

Quest, et al., "A Phorbol Ester Binding Domain of Protein Kinase Cγ" Journal of Biological Chemistry, vol. 269, No. 4, Jan. 28, 1994, pp. 2961–2970.

Bement, et al. "Identification and Overlapping Expression of Multiple Unconventional Myosin Genes In Vertebrate Cell Types" Cell Biology, vol. 91, Jul. 1994, pp. 6549–6553.

Well, et al. "Defective Myosin VIIA Gene Responsible for Usher Syndrome Type 1B" Nature, vol. 374, Mar. 2, 1995, pp. 60–61.

Mooseker, et al. "Unconventional Myosins" Annu. Rev. Cell Dev. Biol., vol. 11, 1995, pp. 633–675.

Reinhard, et al. "A Novel Type of Myosin Implicated In Signaling by rho Family GTPases" The EMBO Journal, vol. 14, No. 4, 1995, pp. 697–704.

Bahler, Martin, "Myosins On the Move to Signal Transduction" Current Opinion in Cell Biology, vol. 8, 1996, pp. 18–22.

Hasson, et al. "Mapping of Unconventional Myosins in Mouse and Human" Genomics, vol. 36, Article No. 0488, 1996, pp. 431–439.

Alignment of Myosin IXa NA with Myosin IXB.

MASPAR Search with CNGC–15 Partial cDNA using Genbank, ESTs Genbank, Patent GeneSeq.

MASPAR Search with Myosin IXa Amino Acid Sequence using Non–Redundant, Patented Genseq, Est Weekly Prot.

MASPAR Search of First 500 Nucleotides of Myosin IXa cDNA using Genbank, ESTs Genbank, Patent GeneSeq, Genetic Inst seqs.

MASPAR Search of Second 500 Nucleotides of Myosin IXa cDNA using Genbank, ESTs Genbank, Patent GeneSeq, Genetic Inst seqs.

MASPAR Search of Third 500 Nucleotides of Myosin IXa cDNA using Genban, ESTs Genbank, Patent GeneSeq, Genetic Inst seqs.

MASPAR Search of Fourth 500 Nucleotides of Myosin IXa cDNA using Genbank, ESTs Genbank, Patent GeneSeq, Genetic Inst seqs.

MASPAR Search of Fifth 500 Nucleotides of Myosin IXa cDNA using Genbank, ESTs Genbank, Patent GeneSeq, Genetic Inst seqs.

MASPAR Search of Sixth 500 Nucleotides of Mysoin IXa cDNA using Genbank, ESTs Genbank, Patent GeneSeq, Genetic Inst seqs.

MASPAR Search of Seventh 500 Nucleotides of Myosin IXa cDNA using Genbank, ESTs Genbank, Patent GeneSeq, Genetic Inst seqs.

MASPAR Search of Eighth 500 Nucleotides of Myosin IXa cDNA using Genbank, ESTs Genbank, Patent GeneSeq, Genetic Inst seqs.

MASPAR Search of Ninth 500 Nucleotides of Myosin IXa cDNA using Genbank, ESTs Genbank, Patent GeneSeq, Genetic Inst seqs.

MASPAR Search of Tenth 500 Nucleotides of Myosin IXa cDNA using Genbank, ESTs Genbank, Patent GeneSeq, Genetic Inst seqs.

MASPAR Search of Eleventh 500 Nucleotides of Myosin IXa cDNA using Genbank, ESTs Genbank, Patent GeneSeq, Genetic Inst seqs.

MASPAR Search of Twelfth 500 Nucleotides of Myosin IXa cDNA using Genbank, ESTs Genbank, Patent GeneSeq, Genetic Inst seqs.

MASPAR Search of Thirteenth 500 Nucleotides of Myosin IXa cDNA using Genbank, ESTs Genbank, Patent GeneSeq, Genetic Inst seqs.

MASPAR Search of Fourteenth 500 Nucleotides of Myosin IXa cDNA using Genbank, ESTs Genbank, Patent GeneSeq, Genetic Inst seqs.

MASPAR Search of Fifteenth 500 Nucleotides of Myosin IXa cDNA using Genbank, ESTs Genbank, Patent GeneSeq, Genetic Inst seqs.

MASPAR Search of Sixteenth 500 Nucleotides of Myosin IXa cDNA using Genbank, ESTs Genbank, Patent GeneSeq, Genetic Inst seqs.

MASPAR Search of Seventeenth 500 Nucleotides of Myosin IXa cDNA using Genbank, ESTs Genbank, Patent GeneSeq, Genetic Inst seqs.

* cited by examiner

| | |
|---|---|
| MNINDGGRRRFEDNEHTLRIYPGAISEGTIYCPIPARKNSTAAEVIESLI | 50 |
| NKLHLDKTKCYVLAEVKEFGGEEWILNPTDCPVQQMMLWPRMALENRLSG | 100 |
| EDYRFLLREKNLDGSIHYGSLQSWLRVTEERRRMMERGFLPQPQQKDFDD | 150 |
| LCSLPDLNEKTLLENLRDRFKHEKIYTYVGSILIVINPFKFLPIYNPKYV | 200 |
| KMYDNHQLGKPEPHIYAVADVAYHAMLQRKKNQCIVISGESGSGKTQSTN | 250 |
| FLIHHLTALSQKGFASGVEQIILGAGPVLEAFGNAKTAHNNNSSRFGKFI | 300 |
| QVNYQETGTVLGAYVEKYLLEKSRLVYQEHNERNYHVFYYLLAGASEDER | 350 |
| SAFHLKQPEEYHYLNQITKKPLRQSWDDYCYDSEPDCFTVEGEDLRHDFE | 400 |
| RLQLAMEMVGFLPKTRRQIFSLLSAILHLGNICYKKKTYRDDSIDICNPE | 450 |
| VLPIVSELLEVKEEMLFEALVTRKTVTVGEKLILPYKLAEAVTVRNSMAK | 500 |
| SLYSALFDWIVFRINHALLNSKDLEHNTKTLSIGVLDIFGFEDYENNSFE | 550 |
| QFCINFANERLQHYFNQHIFKLEQEEYRTEGISWHNIDYIDNTCCINLIS | 600 |
| KKPTGLLHLLDEESNFPQATNQTLLDKFKHQHEDNSYIEFPAVMEPAFII | 650 |
| KHYAGKVKYGVKDFREKNTDHMRPDIVALLRSSKNAFISGMIGIDPVAVF | 700 |
| RWAILRAFFRAMVAFREAGKRNIHRKTGHDDTAPCAILKSMDSFSFLQHP | 750 |
| VHQRSLEILQRCKEEKYSITRKNPRTPLSDLQGMNALNEKNQHDTFDIAW | 800 |
| NGRTGIRQSRLSSGTSLLDKDGIFANSTSSKLLERAHGILTRNKNFKSKP | 850 |
| ALPKHLLEVNSLKHLTRLTLQDRITKSLLHLHKKKKPPSISAQFQASLSK | 900 |
| LMETLGQAEPYFVKCIRSNAEKLPLRFSDVLVLRQLRYTGMLETVQIRQS | 950 |
| GYSSKYSFQDFVSHFHVLLPRNIIPSKFNIQDFFRKINLNPDNYQVGKTM | 1000 |
| VFLKEQERQHLQDLLHQEVLRRIILLQRWFRVLLCRQHFLHLRQASVIIQ | 1050 |
| RFWRNYLNQKQVRDAAVQKDAFVMASAAALLQASWRAHLERQRYLELRAA | 1100 |
| AIVIQQKWRDYYRRRHMAAICIQARWKAYRESKRYQEQRKKIILLQSTCR | 1150 |
| GFRARQRFKALKEQRLRETKPEVGLVNIKGYGSLEIQGSDPSEWEDCSFD | 1200 |
| NRIKAIEECKSVIESNRISRESSVDCLKESPNKQQERAQSQSGVDLQEDV | 1250 |
| LVRERPRSLEDLHQKKVGRAKRESRRMRELEQAIFSLELLKVRSLGGISP | 1300 |
| SEDRRWSTELVPEGLQSPRGTPDSESSQGSLELLSYEESQKSKLESVISD | 1350 |
| EGDLQFPSPKISSSPKFDSRDNALSASNETSSAEHLKDGTMKEMVVCSSE | 1400 |
| SITCKPQLKDSFISNSLPTFFYIPQQDPLKTNSQLDTSIQRNKLLENEDT | 1450 |
| AGEALTLDINRETRRYHCSGKDQIVPSLNTESSNPVLKKLEKLNTEKEER | 1500 |
| QKQLQQQNEKEMMEQIRQQTDILEKERKAFKTIEKPRIGECLVAPSSYQS | 1550 |
| KQRVERPSSLLSLNTSNKGELNVLGSLSLKDAALAQKDSSSAHLPPKDRP | 1600 |
| VTVFFERKGSPCQSSTVKELSKTDRMGTQLNVACKLSNNRISKREHFRPT | 1650 |
| QSYSHNSDDLSREGNARPIFFTPKDNMSIPLVSKEALNSKNPQLHKEDEP | 1700 |
| AWKPVKLAGPGQRETSQRFSSVDEQAKLHKTMSQGEITKLAVRQKASDSD | 1750 |
| IRPQRAKMRFWAKGKQGEKKTTRVKPTTQSEVSPLFAGTDVIPAHQFPDE | 1800 |
| LAAYHPTPPLSPELPGSCRKEFKENKEPSPKAKRKRSVKISNVALDSMHW | 1850 |
| QNDSVQIIASVSDLKSMDEFLLKKVNDLDNEDSKKDTLVDVVFKKALKEF | 1900 |
| RQNIFSFYSSALAMDDGKSIRYKDLYALFEQILEKTMRLEQRDSLGESPV | 1950 |
| RVWVNTFKVFLDEYMNEFKTSDCTATKVPKTERKKRRKKETDLVEEHNGH | 2000 |
| IFKATQYSIPTYCEYCSSLIWIMDRASVCKLCKYACHKKCCLKTTAKCSK | 2050 |
| KYDPELSSRQFGVELSRLTSEDRTVPLVVEKLINYIEMHGLYTEGIYRKS | 2100 |

*Fig. 1A*

```
GSTNKIKELRQGLDTDAESVNLDDYNIHVIASVFKQWLRDLPNPLMTFEL    2150
YEEFLRAMGLQERKETIRGVYSVIDQLSRTHLNTLERLIFHLVRIALQED    2200
TNRMSANALAIVFAPCILRCPDTTDPLQSVQDISKTTTCVELIVVEQMNK    2250
YKARLKDISSLEFAENKAKTRLSLIRRSMGKGRIRRGNYPGPSSPVVVRL    2300
PSVSDVSEETLTSEAAMETDITEQQQAAMQQEERVLTEQIENLQKEKEEL    2350
TFEMLVLEPRASDDETLESEASIGTADSSENLNMESEYAISEKSERSLAL    2400
SSLKTAGKSEPSSKLRKQLKKQQDSLDVVDSSVSSLCLSNTASSHGTRKL    2450
FQIYSKSPFYRAASGNEALGMEGPLGQTKFLEDKPQFISRGTFNPEKGKQ    2500
KLKNVKNSPQKTKETPEGTVMSGRRKTVDPDCTSNQQLALFGNNEFMV     2548
```

*Fig. 1B*

| | | | | | | |
|---|---|---|---|---|---|---|
| GCGTCCGCTC | GCCCGGACCC | TGAGGCTGCT | GGGCCCACCC | TCCCGGAACC | GTCCGACCCT | 60 |
| CGGTGGCCTC | GGCTCGTTCT | GCCATCTCCG | GTCCTACCCT | GGGGCGGAGG | GTGGAAGGCA | 120 |
| GCTTCCGTCG | AAGAGGAGGG | GGCTGCGGTG | GCCACCGCGG | CGGAGCCCGA | GTTATTTTAC | 180 |
| CAAGAAAATG | GTTTGCACGA | CTTTGAACAT | ATACTATCCA | TGCTGATGGG | ACAGGATCCA | 240 |
| ATATGAATAT | AAATGATGGA | GGAAGACGAC | GCTTTGAAGA | TAATGAACAT | ACATTACGGA | 300 |
| TATATCCTGG | GGCTATTTCA | GAAGGGACAA | TCTACTGTCC | GATTCCTGCC | AGAAAAAACT | 360 |
| CCACAGCTGC | TGAGGTGATT | GAGTCTCTTA | TAAACAAACT | TCATCTTGAC | AAAACAAAAT | 420 |
| GTTACGTTCT | AGCAGAGGTA | AAGGAATTTG | GTGGAGAAGA | ATGGATTCTC | AATCCAACAG | 480 |
| ATTGTCCAGT | TCAGCAAATG | ATGCTGTGGC | CCCGAATGGC | TCTGGAAAAT | CGCTTAAGTG | 540 |
| GAGAAGACTA | CCGCTTCCTT | CTGAGAGAGA | AAAACCTTGA | TGGATCAATC | CATTATGGTA | 600 |
| GCCTGCAGTC | ATGGCTACGG | GTAACAGAAG | AACGTCGCAG | GATGATGGAA | CGGGGTTTTC | 660 |
| TTCCACAGCC | TCAACAGAAA | GACTTTGATG | ATTTATGTAG | TTTACCTGAT | TTGAATGAGA | 720 |
| AAACTCTCTT | AGAAAACCTA | CGAGATCGCT | TTAAGCATGA | AAAAATTTAT | ACCTATGTTG | 780 |
| GCAGTATTCT | AATAGTTATT | AACCCATTCA | AGTTTCTTCC | TATTTATAAC | CCCAAATATG | 840 |
| TCAAAATGTA | TGATAACCAC | CAACTGGGAA | AACCTGAGCC | CCACATTTAT | GCTGTGGCTG | 900 |
| ATGTAGCTTA | TCATGCCATG | CTTCAGCGCA | AAAAGAATCA | GTGCATCGTG | ATTTCAGGAG | 960 |
| AGAGTGGTTC | TGGGAAGACT | CAAAGCACAA | ACTTTCTTAT | TCACCACCTT | ACTGCTCTCA | 1020 |
| GTCAGAAAGG | ATTTGCCAGT | GGAGTAGAAC | AGATTATTCT | TGGAGCTGGA | CCAGTACTTG | 1080 |
| AGGCCTTTGG | AAATGCAAAG | ACAGCTCATA | ATAACAATTC | AAGTCGTTTT | GGGAAGTTTA | 1140 |
| TTCAAGTAAA | TTACCAGGAA | ACAGGCACTG | TACTTGGTGC | CTATGTTGAA | AAATATCTAC | 1200 |
| TGGAGAAGTC | CAGACTCGTT | TATCAGGAGC | ATAATGAACG | GAACTATCAT | GTATTCTATT | 1260 |
| ACCTCCTGGC | AGGAGCAAGT | GAAGATGAGA | GATCAGCATT | CCATCTTAAG | CAACCAGAGG | 1320 |
| AATATCATTA | TCTCAATCAG | ATAACAAAGA | AACCCCTCAG | ACAGAGCTGG | GATGATTATT | 1380 |
| GCTATGACTC | TGAGCCGGAT | TGCTTCACGG | TGGAAGGAGA | AGATTTGAGA | CATGACTTTG | 1440 |
| AGCGCCTACA | ACTTGCCATG | GAAATGGTAG | GATTTCTTCC | CAAGCACGA | AGACAGATTT | 1500 |
| TCTCTCTTCT | CTCAGCCATA | CTACATTTGG | GTAATATCTG | TTACAAAAAG | AAGACATACC | 1560 |
| GGGATGACTC | CATTGATATC | TGTAATCCTG | AAGTTCTGCC | TATTGTCTCA | GAATTATTAG | 1620 |
| AGGTTAAAGA | AGAGATGCTA | TTTGAAGCAT | TAGTTACAAG | GAAGACGGTG | ACAGTGGGAG | 1680 |
| AAAAGCTTAT | TTTGCCATAC | AAGTTGGCAG | AGGCTGTGAC | AGTGAGGAAC | TCCATGGCTA | 1740 |
| AGTCTCTGTA | TAGTGCCCTG | TTTGACTGGA | TAGTTTTTCG | AATTAATCAT | GCACTTCTGA | 1800 |
| ATAGTAAAGA | TTTAGAGCAT | AATACCAAGA | CATTGTCTAT | TGGTGTTCTT | GATATTTTTG | 1860 |
| GGTTTGAAGA | TTATGAAAAT | AACAGCTTTG | AACAGTTCTG | TATTAATTTT | GCTAATGAAC | 1920 |
| GTTTACAGCA | CTACTTTAAT | CAGCATATCT | TTAAATTGGA | ACAAGAGGAA | TATAGAACTG | 1980 |
| AAGGTATCAG | CTGGCACAAC | ATAGATTACA | TTGATAATAC | CTGCTGCATA | AATCTTATTA | 2040 |
| GCAAAAAACC | AACAGGACTG | CTTCATCTTT | TGGATGAAGA | AAGCAACTTT | CCACAGGCTA | 2100 |
| CAAATCAAAC | ATTGCTAGAC | AAGTTTAAGC | ATCAACATGA | AGATAATTCT | TACATCGAAT | 2160 |
| TTCCAGCCGT | GATGGAGCCT | GCTTTCATTA | TAAAACATTA | TGCTGGAAAA | GTAAAATATG | 2220 |
| GGGTAAAGGA | TTTCCGGGAA | AAAAATACAG | ATCATATGCG | CCCAGACATT | GTAGCTCTTC | 2280 |
| TGAGAAGCAG | CAAGAATGCA | TTTATCTCTG | GGATGATTGG | AATTGATCCT | GTAGCTGTTT | 2340 |
| TCCGATGGGC | AATTCTCCGA | GCTTTTTTCA | GAGCCATGGT | TGCTTTCAGG | GAAGCTGGGA | 2400 |

*Fig. 2A*

```
AAAGAAACAT TCACAGAAAA ACTGGACATG ATGATACAGC GCCATGTGCA ATTTTGAAAA    2460
GTATGGATAG TTTTAGCTTT CTCCAACACC CAGTCCACCA GAGGAGCTTA GAGATTCTGC    2520
AGAGATGCAA GGAAGAGAAG TACAGTATAA CCCGGAAAAA TCCCAGAACA CCTCTTTCTG    2580
ATCTCCAGGG CATGAATGCT CTAAATGAAA AAAACCAACA TGATACATTT GATATTGCCT    2640
GGAATGGCAG AACTGGGATT CGCCAGAGCA GACTATCAAG TGGCACCTCC TTGCTTGATA    2700
AAGATGGAAT ATTTGCTAAT TCAACTAGCA GCAAACTCCT GGAGAGAGCC CATGGAATTC    2760
TCACGAGAAA CAAAAATTTC AAATCCAAGC CTGCCCTTCC AAAGCACTTG CTAGAAGTAA    2820
ATTCTTTAAA GCACCTGACA AGACTGACAC TACAAGATCG CATTACCAAG TCTCTTCTTC    2880
ATTTACACAA GAAGAAAAAA CCTCCCAGCA TCAGTGCCCA GTTTCAGGCA TCATTAAGCA    2940
AGCTAATGGA AACACTTGGT CAAGCAGAAC CATATTTTGT AAAATGCATT CGCTCTAATG    3000
CTGAAAAGCT GCCCTTAAGG TTCAGTGATG TCTTGGTACT TAGACAGCTT CGATACACCG    3060
GGATGCTGGA AACAGTTCAA ATTCGCCAAT CAGGATACAG CTCCAAATAT TCTTTCCAGG    3120
ATTTTGTGAG CCACTTCCAT GTACTTCTTC CCCGAAATAT TATTCCATCC AAATTTAACA    3180
TTCAGGATTT CTTCAGGAAA ATAAATCTTA ATCCAGATAA TTATCAAGTT GGAAAAACCA    3240
TGGTCTTTCT AAAGGAGCAG GAACGACAGC ACTTACAAGA TCTGCTTCAC CAAGAGGTGC    3300
TCCGCAGAAT CATATTGTTG CAGCGATGGT TCAGGGTCTT GCTGTGTAGG CAGCATTTCC    3360
TCCATCTGAG ACAAGCATCT GTTATTATCC AGAGATTCTG GAGGAATTAC CTAAATCAGA    3420
AGCAAGTCAG AGATGCAGCT GTGCAGAAGG ATGCTTTTGT TATGGCTAGT GCAGCTGCTC    3480
TTCTCCAAGC TTCCTGGCGT GCTCACTTAG AGAGGCAGCG GTACTTGGAG TTACGGGCTG    3540
CAGCCATCGT TATCCAGCAG AAATGGAGAG ATTACTATAG GCGCAGGCAC ATGGCTGCTA    3600
TTTGCATACA AGCAAGATGG AAAGCCTACA GGGAAAGTAA AAGGTACCAA GAACAAAGGA    3660
AAAAAATTAT CCTTTTGCAA TCAACATGTA GAGGATTCAG AGCAAGACAA AGATTTAAAG    3720
CTTTAAAAGA ACAAAGGCTA AGAGAAACAA AGCCAGAAGT TGGATTGGTG AATATTAAGG    3780
GATATGGATC TCTGGAAATT CAGGGTTCAG ACCCTTCAGA ATGGGAGGAT TGTTCTTTTG    3840
ACAACAGAAT AAAAGCCATA GAGGAATGTA AATCTGTAAT AGAGAGTAAT CGAATTAGCC    3900
GTGAAAGTTC AGTGGACTGC TTGAAGGAGT CACCAAACAA GCAGCAGGAG AGAGCCCAAA    3960
GCCAGAGTGG TGTGGACTTG CAGGAAGATG TGCTTGTAAG AGAGAGACCC AGGTCCTTGG    4020
AGGATCTCCA TCAGAAAAAA GTAGGCCGGG CTAAGAGAGA AAGTAGGAGA ATGAGAGAAC    4080
TAGAGCAAGC TATATTTAGC TTAGAATTGC TGAAAGTTCG TTCTCTTGGT GGTATTTCTC    4140
CTTCAGAGGA TCGCAGATGG TCTACAGAAT TGGTGCCTGA AGGCCTTCAG TCTCCACGGG    4200
GTACACCTGA TAGTGAGAGC TCTCAAGGAA GCTTGGAACT TCTGAGCTAT GAGGAAAGCC    4260
AAAAGAGCAA ACTAGAGTCT GTCATTTCAG ATGAAGGAGA CTTGCAGTTT CCATCACCTA    4320
AGATATCCAG CAGTCCAAAA TTTGATTCAC GGGACAATGC CCTCAGTGCC TCAAATGAGA    4380
CTAGCAGTGC AGAGCATTTG AAGGATGGAA CTATGAAGGA AATGGTGGTC TGCAGTTCTG    4440
AGTCTATTAC CTGTAAACCA CAGCTGAAAG ACTCCTTCAT TTCAAATAGT CTACCTACTT    4500
TTTTTTATAT CCCCCAACAA GACCCACTGA AAACAAATTC CCAACTAGAC ACAAGTATCC    4560
AAAGAAACAA ACTATTGGAA AATGAAGACA CAGCGGGGGA AGCTCTTACT TTGGATATCA    4620
ACAGGGAAAC TAGAAGGTAT CACTGCTCAG GAAAAGATCA GATTGTTCCT TCTTTGAATA    4680
CAGAGTCTTC TAATCCTGTG CTTAAGAAGT TAGAAAAGCT AAACACTGAG AAGGAAGAAA    4740
GGCAAAAACA GTTGCAGCAA CAGAATGAAA AAGAGATGAT GGAACAGATT CGCCAGCAAA    4800
```

*Fig. 2B*

```
CAGATATTTT AGAGAAGGAG CGCAAAGCCT TCAAGACAAT TGAAAAGCCA AGAATTGGAG    4860
AGTGTTTGGT GGCACCATCT TCCTATCAGT CAAAGCAAAG AGTAGAGAGG CCATCCTCTC    4920
TCCTCAGCTT AAATACCTCA AATAAGGGAG AACTTAATGT ACTGGGGTCC CTATCATTAA    4980
AAGATGCAGC TCTTGCCCAA AAAGACAGTT CCTCTGCTCA CTTACCCCCA AAGGACCGAC    5040
CTGTCACCGT GTTCTTTGAA AGAAAAGGAA GTCCATGCCA ATCTAGTACT GTCAAGGAAT    5100
TATCCAAGAC AGACAGAATG GGCACCCAGC TGAATGTAGC CTGTAAACTC TCAAATAATC    5160
GCATTTCAAA AAGAGAACAC TTTAGGCCAA CTCAGTCTTA CAGCCACAAT TCTGATGACC    5220
TTTCCAGAGA GGGAAATGCT AGGCCCATTT TCTTCACTCC AAAGGATAAT ATGAGTATTC    5280
CCCTTGTCAG CAAAGAAGCC TTAAACAGTA AAAATCCTCA ACTCCATAAA GAAGATGAAC    5340
CAGCATGGAA ACCTGTGAAG TTAGCTGGGC CAGGCCAAAG AGAGACATCA CAGCGATTTT    5400
CGTCAGTTGA TGAACAAGCA AAACTTCATA AGACTATGTC TCAAGGAGAG ATTACCAAGT    5460
TGGCAGTGAG ACAGAAGGCT TCAGATTCAG ATATAAGACC TCAGAGAGCT AAGATGAGAT    5520
TCTGGGCCAA AGGGAAACAA GGGGAGAAGA AGACTACCAG AGTGAAACCT ACTACCCAGT    5580
CAGAGGTTTC GCCACTCTTT GCAGGCACAG ATGTGATTCC AGCTCATCAG TTTCCAGATG    5640
AATTAGCTGC ATATCACCCA ACACCTCCTT TGAGCCCAGA ACTGCCCGGC AGTTGCCGGA    5700
AGGAATTCAA AGAGAACAAA GAACCTTCTC CAAAGGCTAA GCGCAAGCGA AGTGTGAAGA    5760
TTAGCAACGT GGCTTTGGAT TCTATGCATT GGCAAAATGA CTCTGTCCAG ATCATAGCAA    5820
GTGTCAGTGA TTTAAAAAGC ATGGATGAAT TTCTTCTGAA AAAGGTGAAT GACCTAGATA    5880
ATGAAGACAG CAAGAAGGAT ACACTAGTGG ATGTTGTATT TAAAAAAGCC CTGAAGGAAT    5940
TTCGGCAGAA TATCTTCAGC TTTTATTCAT CTGCATTGGC GATGGATGAT GGGAAAAGCA    6000
TACGGTATAA AGACCTCTAT GCACTATTTG AACAGATTCT GGAAAAGACG ATGAGGCTTG    6060
AGCAGCGTGA TTCACTGGGT GAATCTCCAG TGAGAGTTTG GGTCAACACT TTTAAAGTGT    6120
TTTTAGATGA ATATATGAAT GAATTCAAGA CTTCAGATTG CACAGCCACA AAGGTGCCAA    6180
AAACAGAAAG AAAGAAAAGA AGGAAAAAGG AAACTGATTT GGTGGAAGAA CACAATGGTC    6240
ACATCTTTAA AGCCACCCAA TATAGCATCC CTACATACTG TGAATACTGT TCTTCTTTGA    6300
TATGGATAAT GGACCGAGCC TCTGTTTGCA AATTATGCAA GTATGCTTGC CATAAGAAGT    6360
GCTGTCTGAA AACCACAGCC AAGTGCTCTA AAAAGTATGA TCCAGAGCTG TCATCTCGAC    6420
AATTTGGGGT TGAACTGTCC CGTTTGACCA GTGAAGACCG AACTGTTCCT TTAGTAGTGG    6480
AAAAGCTCAT AAACTACATT GAAATGCATG GACTGTATAC AGAAGGTATT TATCGAAAGT    6540
CTGGTTCGAC TAATAAAATC AAGGAGCTTC GGCAGGGTCT AGATACAGAT GCTGAGAGTG    6600
TAAATCTAGA TGACTATAAC ATACACGTCA TTGCAAGTGT ATTCAAACAA TGGCTTCGAG    6660
ATTTGCCCAA TCCTCTCATG ACCTTTGAAC TCTATGAGGA ATTTCTTCGA GCTATGGGCC    6720
TTCAGGAGAG GAAGGAGACA ATCCGTGGTG TATACTCTGT GATTGATCAA CTCTCCCGAA    6780
CTCATCTCAA TACACTGGAA CGCCTCATCT TTCATCTAGT CAGGATTGCT CTGCAGGAAG    6840
ACACTAATCG AATGTCTGCT AATGCTTTGG CCATTGTGTT TGCGCCCTGC ATTCTCCGCT    6900
GCCCTGACAC CACTGACCCA CTACAAAGTG TACAGGACAT CAGTAAGACT ACCACTTGTG    6960
TGGAACTGAT TGTTGTGGAA CAAATGAATA AATACAAGGC TCGTCTCAAA GATATCAGTA    7020
GCTTGGAATT TGCTGAGAAT AAGGCAAAGA CCAGGTTGTC ACTGATTCGT AGATCAATGG    7080
GAAAGGGGCG TATTCGTCGA GGAAACTATC CAGGTCCATC GTCTCCTGTT GTAGTTCGGT    7140
TGCCTTCTGT GTCTGATGTC TCAGAGGAGA CCTTGACTAG TGAGGCAGCC ATGGAGACTG    7200
```

*Fig. 2C*

```
ACATCACAGA ACAGCAGCAA GCAGCTATGC AGCAGGAGGA GAGAGTACTG ACTGAGCAGA    7260
TTGAGAACCT ACAGAAGGAG AAGGAGGAGC TAACATTTGA GATGCTTGTA CTGGAACCCC    7320
GTGCCTCTGA TGATGAAACC CTTGAGTCTG AGGCCTCCAT TGGGACTGCT GATAGCTCAG    7380
AGAATTTGAA TATGGAGTCT GAATATGCTA TCTCTGAGAA ATCAGAAAGA AGCTTAGCCC    7440
TTAGCTCCCT GAAGACAGCT GGCAAGTCTG AACCTTCCAG CAAGTTGCGA AAGCAACTTA    7500
AAAAGCAGCA AGACTCTTTA GATGTCGTGG ACTCTTCGGT CTCCTCTTTA TGTCTGTCTA    7560
ACACGGCATC ATCTCATGGG ACCAGAAAAC TATTTCAGAT TTATTCCAAA TCTCCATTCT    7620
ACCGAGCTGC CTCAGGTAAT GAGGCCCTGG GAATGGAAGG ACCATTGGGC CAGACCAAAT    7680
TCCTGGAAGA CAAGCCTCAG TTCATCAGCA GAGGAACCTT CAACCCGGAA AAGGGCAAAC    7740
AAAAATTAAA GAATGTGAAA AACTCACCTC AGAAAACCAA AGAGACCCCA GAGGGGACAG    7800
TCATGTCTGG CCGCAGAAAA ACTGTGGACC CAGACTGCAC CTCCAACCAA CAGCTAGCAC    7860
TCTTTGGAAA TAATGAATTT ATGGTCTGAA CCGGCAGATG TGTGTCCCTC CGTGGCTACA    7920
GAGTGGTAAA CAAATCTCAC CTTTGGGGCT GCGTTTCATC ACCTCGTCCA CAATAGTCAA    7980
TCCTAATTGT GGTCCTGCCT CTTTTCTAAG CATATGGCTA AGACTGTATG TGCTGAATTC    8040
CTGGGCCTCC TGCAGAAGCA GAAAGCCTGC TGGGGATGGT GCCAGCTGTG CCTTGGCTGT    8100
TGTATTTGAA TTGAGATTTT TACTATACAA AGCCACCTAG GGCCTGGGGA TTTGGGTCAG    8160
TTGTAGTTGC CTCTCCCCCA CCCTCTTTTC CCTTCCCAAA GGTGGGTGTT GAACTAGGGG    8220
GGATATTGCT GTCCTGAGGG ACCCTCTCAT TTCTGACATT TGAAGAAAAC GTATAAATCT    8280
TTCTTAACCG TGAAAGCAAA AGCCTTTGGG TTTATTTTGG GATAGTTAGG AGCTAGGGTA    8340
GAATATAATT TTTTTCCAAA AACTTACTTA CAAACAAAAA GCCTAATCCC TCTATTTTAA    8400
GATTTCTGAA AAAACACTCC ATGTTATATT CTGGGGAAAG CAAAAACAAA AAAAAAAAA     8460
AAAAAAAAAA AAA                                                      8473
```

*Fig. 2D*

```
GAATTCGGGC TTCCATCCTT AATAGGAACT CAATNNTAGG GCTNGGGCGG CCGCCCGGGC   60
AGGTGCGCGA ACAGGAGAGG GTCAAGTCGG CCGGATTTTG GATTATCCAC CCCTACAGTG  120
ACTTCAGATT TTACTGGGAC CTGACCATGC TGCTGCTGAT GGTGGGAAAC CTGATTATCA  180
TTCCTGTGGG CATCACCTTC TTCAAGGATG AGAACACCAC ACCCTGGATT GTCTTCAATG  240
TGGTGTCAGA CACATTCTTC CTCATCGACT TGGTCTTCAA CTTCCGCACA GGGATCGTGG  300
TGGAGGACAA CACAGAGATC ATCCTGGACC CGCAGCGGAT TAAAATGAAG TACCTGAAAA  360
GCTGGTTCAT GGTAGATTTC ATTTCCTCCA TCCCCCGTGG AAAACATCTT CCTCATTGTG  420
GAGACAGGCA TCGACTCGGA GGTCTACAAG ACTGCCCGGG CCCTGCGCAT TGTCCGCTTC  480
ACGAAGATCC TCAGCCTCTT ACGCCTGTTA CGCCTCTCCC GCCTCATTCG ATATATTCAC  540
CAGTGGGAAG AGATCTTCCA CATGACCTAC GACCTGGCCA GCGCCGTGGT GCGCATCGTG  600
AACCTCATCG GCATGATGCT CCTGCTCTGC CACTGGGACG GCTGCCTGCA GTTCCTGGTA  660
CCCATGCTAC AGGACTTCCC TGACGACTGC TGGGTGTCCA TCAACAACAT GGTGAACAAC  720
TCCTGGGGGA AGCAGTACTC CTACGCGCTC TTCAAGGCCA TGAGCCACAT GCTGTGCATC  780
GGCTACGGGC GGCAGGCGCC CGTGGGCATC TCCGACGTCT GGCTCACCAT GCTCAGCATG  840
ATCGTGGGTG CCACCTGCTA CGCCATGTTC ATTGGCCACG CCACTGCCCT CATCCAGTCC  900
CTGGACTCCT CCCGGCGCCA GTACCAGGAA AAGTACAAGC AGGTGGAGCA GTACATGTCC  960
TTTCACAAGC TCCCGCCCGA CACCCGGCAG CGCATCCACG ACTACTACGA GCACCGCTAC 1020
CAGGGCAAGA TGTTCGACGA GGAGAGCACC CTGGGCGAGC TAAGCGAGCC CCTGCGGGAG 1080
GAGATCATCA ACTTTAACTG TCGGAAGCTG GTGGCCTCCA TGCCACTGTT TGCCAATGCG 1140
GACCCCAACT TCGTGACGTC CATGCTGACC AAGCTGCGTT TCGAGGTCTT CCAGCCTGGG 1200
GACTACATCA TCCGGGAAGG CACCATTGGC AAGAAGATGT ACTTCATCCA GCATGGCGTG 1260
GTCAGCGTGC TCACCAAGGG CAACAAGGAG ACCAAGAAGC CGAATTC             1307
```

MYOSIN IXA AND CYCLIC NUCLEOTIDE GATED CHANNEL-15 (CNGC-15) POLYNUCLEOTIDES, POLYPEPTIDES, COMPOSITIONS, METHODS, AND USES THEREOF

CROSS-REFERENCE TO RELATED APPLICATIONS

This application claims the benefit of U.S. Provisional Application Ser. No. 60/062,858, filed Oct. 15, 1997, U.S. Provisional Application No. 60/062,241, filed Oct. 17, 1997, and U.S. Provisional Application No. 60/068,953, filed Dec. 30, 1997, the contents of which are herein incorporated by reference.

FIELD OF THE INVENTION

This invention relates to the fields of molecular biology and pharmaceutical research. More specifically, this invention relates to the identification and recombinant expression of two new genes, cyclic nucleotide gated channel-15 (CNGC-15) and Myosin IXa. Accordingly, isolation of the human myosin IXa gene will prove useful in the study, diagnosis and treatment of Bardet-Biedl Syndrome, Usher Syndrome and related conditions.

BACKGROUND OF THE INVENTION

Usher Sydrome type1 (USH1) is characterized by a profound congenital sensoneural hearing loss, vestibular dysfinction and prepubescent onset retinitis pigmentosa. Family studies indicated that three genes with different chromosomal locations are responsible for USH1; a defect in any one of these genes causes the disease. Of these, the gene USH1B mapped to a region homologous to the murine region containing the mouse deafness mutant shaker-1 which results from mutations in myosin VIIa. Subsequent work confirmed that myosin VIIa is the cause of Usher Sydrome type 1B and localized the myosin VIIa protein to the receptor cells of the inner ear (Hasson et al. (1995) *Genomics* 36:431–439) and the connecting cilia of photoreceptor cells in the retina (Liu et al. (1997) *Cell Motil. Cytoskel.* 37:240–252).

Retinitis pigmentosa is also associated with Bardet-Biedl Syndrome. Bardet-Biedl Syndrome is further characterized by obesity, retinal degeneration, syndactyly and/or polydactyly, hypogenitalism and mental retardation (Schachat et al. (1982) *Arch. Ophthalmol.* 100:285–288; Green et al. (1989) *N. Engl. J. Med.* 321:1002–1009) and can result from aberrations in one of at least four different genes. Other publications relating to myosin IXa include Bruford et al. (1997) *Genomics* 41:93–99 and Bement et al. (1994) *Proc. Natl. Acad. Sc. USA* 91:6549–6553.

All references cited herein are incorporated by reference.

SUMMARY OF THE INVENTION

The present invention discloses the amino acid and nucleic acid sequences of a new Cyclic nucleotide gated channel (CNGC) and Myosin that map to the region of the human chromosome associated with Bardet-Biedl Syndrome. CNGCs comprise a family of multimeric protein ion channels that open in response to the binding of a cyclic nucleotide to an intracellular domain. The two new proteins, CNGC-15 and Myosin IXa, are useful in the study, diagnosis and treatment of Bardet-Biedl Syndrome and Usher Syndrome. Other indications that can be treated by CNGC-15 and/or Myosin IXa polypeptides, or agonists or antagonists include hearing loss, retinis pigmentosa, obesity, hypogonadism, sterility, polydactyly, brachydactyly, syndactyly, mental retardation, renal abnormalities, hypertension, diabetes and cardiovascular abnormalities.

Compositions and methods for expressing cyclic nucleotide gated channel-15 (CNGC-15) and Myosin IXa are provided. The compositions comprise CNGC-15 and Myosin IXa polypeptides and derivatives thereof, nucleotide sequences, expression cassettes, transformed cells and antibodies to these polypeptides. Methods for the expression and detection of CNGC-15 and Myosin IXa nucleotides and polypeptides and compositions for the treatment of these conditions are provided.

BRIEF DESCRIPTION OF THE FIGURES

FIG. 1 sets forth the amino acid sequence of the human Myosin IXa polypeptide (SEQ ID NO: 1).

FIG. 2 sets forth the nucleotide sequence of the human Myosin IXa cDNA (SEQ ID NO: 2). The ATG translational intiation codon at position 243 and the TGA translational stop codon at position 7887 are underlined.

FIG. 3 sets forth the nucleotide sequence of a human CNGC-15 partial cDNA (SEQ ID NO: 3).

DETAILED DESCRIPTION OF THE INVENTION

The present invention is drawn to compositions and methods useful in the treatment of Bardet-Biedl Syndrome, Usher Syndrome, hearing loss, retinis pigmentosa, obesity, hypogonadism, sterility, polydactyly, brachydactyly, syndactyly, mental retardation, renal abnormalities, hypertension, diabetes and cardiovascular abnormalities. More particularly, two new polypeptides and the genes encoding them, CNGC-15 and Myosin IXa, have been identified that are useful in the treatment of these and a variety of other conditions. The human Myosin IXa polypeptide and cDNA are shown in FIGS. 1 and 2, as SEQ ID NO: 1 and SEQ ID NO: 2, respectively. The human CNGC-15 partial cDNA is shown in FIG. 3 as SEQ ID NO: 3.

Thus, it is an object of the invention to provide native CNGC-15 and Myosin IXa substantially free of other human proteins.

Another object of the invention is to provide polypeptides that are mutants, fragments and derivatives of CNGC-15 or Myosin Ixa. Regions of particular importance of Myosin IXa include: the open reading frame (nucleotides 243–7886 of SEQ ID NO: 2) encoding a 2548 amino acid protein (SEQ ID NO: 1); the N-terminal extension (residues 1–146 of SEQ ID NO: 1) encoded by nucleotides 243–680 of SEQ ID NO: 2; the head domain (residues 147–719 of SEQ ID NO: 1) encoded by nucleotides 683–2399 of SEQ ID NO: 2; the ATP binding loop (residues 239–246 of SEQ ID NO: 1) encoded by nucleotides 959–977 of SEQ ID NO: 2; the minimal length 2nd insert (residues 720–835 of SEQ ID NO: 1) encoded by nucleotides 2402–2747 of SEQ ID NO: 2; the light chain binding domain (residues 972–1166 of SEQ ID NO: 1) encoded by nucleotides 3158–3740 of SEQ ID NO: 2; and the GAP domain (residues 2074–2219) of SEQ ID NO: 1 encoded by nucleotides 6473–6899 of SEQ ID NO: 2.

Accordingly, the invention provides a Myosin IXa polypeptide comprising an amino acid sequence selected from the group consisting of:

a) SEQ ID NO: 1;
b) residues 1–146 of SEQ ID NO: 1;
c) residues 147–719 of SEQ ID NO: 1;
d) residues 239–246 of SEQ ID NO: 1;
e) residues 720–835 of SEQ ID NO: 1;
f) residues 972–1166 ofSEQ ID NO: 1;
g) residues 2074–2219 of SEQ ID NO: 1;

h) a polypeptide having at least about 61% homology to SEQ ID NO:1;

i) a polypeptide having at least about 95% homology to an amino acid sequence of b), c), d), e), f) or g); and j) a polypeptide of at least about 90 contiguous residues of SEQ ID NO: 1.

The Myosin IXa polypeptides of the invention will have at least about 61% homology to SEQ ID NO:1, preferably at least about 70% homology, more preferably at least about 80% homology and most preferably at least about 90% homology. The polypeptides of b), c), d), e), f) or above, will have at least about 95% homology to SEQ ID NO:1, more preferably at least about 96% homology, even more preferably at least about 97% homology and most preferably at least about 98% homology.

Similarly, the invention provides a CNGC-15 polypeptide comprising an amino acid sequence selected from the group consisting of:

a) a polypeptide encoded by SEQ ID NO: 3;

b) a polypeptide encoded by nucleotides 369–1307 of SEQ ID NO: 3;

c) a polypeptide having at least about 80% homology to the polypeptide encoded by nucleotides 369–1307 of SEQ ID NO: 3; and d) a polypeptide of at least about 20 contiguous residues of the polypeptide encoded by nucleotides 369–1307 of SEQ ID NO: 3.

The CNGC-15 polypeptides of the invention will have at least about 70% homology to a), b), c) or d) above, preferably at least about 80% homology, more preferably at least about 85% homology and most preferably at least about 90% homology.

In another aspect of the invention provides a chimeric polypeptide comprising a CNGC-15 polypeptide, or fragment thereof and a polypeptide of interest. Similarly, the invention provides a chimeric polypeptide comprising a Myosin IXa polypeptide, or fragment thereof, fused to a polypeptide of interest. Nucleotide sequences encoding chimeric CNGC-15 and Myosin IXa polypeptides are also provided.

Yet another object of the invention is to provide polynucleotides that encode the mutants, fragments, and derivatives, as well as the native CNGC-15 and Myosin IXa. Accordingly, the invention provides an isolated nucleotide sequence selected from the group consisting of:

a) a nucleotide sequence encoding a native Myosin IXa polypeptide;

b) a nucleotide sequence encoding the amino acid sequence of SEQIDNO: 1;

c) the nucleotide sequence of SEQ ID NO: 2;

d) a nucleotide sequence comprising at least about 390 contiguous bases of SEQ ID NO: 2;

e) a nucleotide sequence comprising nucleotides 243–7085 of SEQ ID NO: 2;

f) a nucleotide sequence comprising nucleotides 243–680 of SEQ ID NO: 2;

g) a nucleotide sequence comprising nucleotides 683–2399 of SEQ ID NO: 2;

h) a nucleotide sequence comprising nucleotides 959–977 of SEQ ID NO: 2;

i) a nucleotide sequence comprising nucleotides 2402–2747 of SEQ ID NO: 2;

j) a nucleotide sequence comprising nucleotides 3158–3740 of SEQ ID NO: 2; and k) a nucleotide sequence comprising nucleotides 6473–6899 of SEQ ID NO: 2.

The invention similarly provides an isolated nucleotide sequence selected from the group consisting of:

a) a nucleotide sequence encoding a native CNGC-15 polypeptide;

b) a nucleotide sequence encoding the polypeptide encoded by nucleotides 369–1307 of SEQ ID NO: 3;

c) the nucleotide sequence of SEQ ID NO: 3;

d) a nucleotide sequence comprising at least 45 contiguous nucleotides of the sequence of SEQ ID NO:3; and e) a nucleotide sequence that hybridizes under stringent conditions to a denatured DNA having a nucleotide sequence of a), b), c) or d).

These polynucleotides can be operably linked to heterologous promoters to form expression cassettes. The expression cassettes can be introduced into suitable host cells for expression of CNGC-15 and/or Myosin IXa polypeptides and derivatives thereof.

Another object of the invention is to provide a transformed cell transiently expressing or having stably incorporated into its genome an expression vector comprising a promoter operably linked to a nucleotide sequence encoding a CNGC-15 or Myosin IXa polypeptide, or a fragment, derivative mutant or fusion thereof.

A further object of the invention is to provide a methJd for producing a CNGC-15 or Myosin IXa polypeptide or a derivative thereof, comprising:

a) providing a host cell transiently or stably transformed with an expression vector comprising a promoter operably linked to a nucleotide sequence encoding said CNGC-15 or Myosin IXa polypeptide or derivative thereof; and b) culturing the host cell under conditions which allow expression of said polypeptide.

Another object of the invention is to provide a method for detecting CNGC-15 polynucleotides. The method comprises:

a) providing a nucleic acid probe which hybridizes to a nucleotide encoding a CNGC-15 polypeptide or a mutant, fragment or derivative thereof;

b) contacting the probe with a sample of polynucleotides under hybridizing conditions to form a duplex; and c) detecting said duplexes.

A further object of the invention is to provide a method for detecting unconventional Myosin polynucleotides. The method comprises:

a) providing a nucleic acid probe which hybridizes to a nucleotide encoding a Myosin IXa or a mutant, fragment or derivative thereof;

b) contacting the probe with a sample of polynucleotides under hybridizing conditions to form a duplex; and c) detecting said duplexes.

Yet another object of the invention is to provide antibodies to the CNGC-15 and Myosin IXa polypeptides.

Another object of the invention is to provide a method for detecting CNGC-15 polypeptides. The method comprises:

a) providing an antibody that binds to a CNGC-15 polypeptide;

b) contacting the antibody to a sample under binding conditions to form a duplex; and c) detecting said duplexes.

Still another object of the invention is to provide a method for detecting Myosin IXa polypeptides. The method comprises:

a) providing an antibody that binds to a Myosin IXa polypeptide;
b) contacting the antibody to a sample under binding conditions to form a duplex; and
c) detecting said duplexes.

The invention further provides a method for treating Bardet-Biedl Syndrome, Usher Syndrome, hearing loss, retinis pigmentosa, obesity, hypogonadism, sterility, polydactyly, brachydactyly, syndactyly, mental retardation, renal abnormalities, hypertension, diabetes and cardiovascular abnormalities, comprising administering a therapeutically effective amount of a CNGC-15 or Myosin IXa polypeptide, or derivative thereof to a subject in need of such treatment. In still another aspect, the invention provides a composition comprising CNGC-15 or Myosin IXa or an active derivative thereof, and a pharmaceutically acceptable carrier.

Modes for Carrying Out the Invention

A. Definitions

As used herein, the terms "native CNGC-15" and "native Myosin IXa" refer to the polypeptides found in nature. for example, native CNGC-15 and native Myosin IXa are polypeptides with substantial amino acid sequence identity to SEQ ID NO: 1 and SEQ ID NO: 3, respectively. This definition includes allelic variants and other naturally occurring modifications of SEQ ID NO: 1 and SEQ ID NO: 3.

"CNGC-15 polypeptides" and "Myosin IXa polypeptides" include mutants, fragments, derivatives and fusions as well as the native CNGC-15 or Myosin IXa.

"Mutants" of the native CNGC-15 or Myosin IXa are polypeptides having an amino acid sequence which retain at least about 50% amino acid sequence identity with SEQ ID NO: 1 or SEQ ID NO: 3, respectively; more typically, at least about 60%; even more typically, at least about 80%. Preferably mutants will retain at least about 85% amino acid sequence identity with SEQ ID NO: 1 or SEQ ID NO: 3; more preferably, at least about 90%; even more preferably, at least about 95%. These differences may be conservative amino acid substitutions, insertions or deletions in the amino acid sequence.

"Fragments" possess the same amino acid sequence of the native or mutant CNGC-15 or Myosin IXa polypeptides except the fragments lack the amino and/or carboxyl terminal sequences of the native or mutant polypeptide.

"Derivatives" possess the same amino acid sequence of the native, mutant or fragment CNGC-15 and Myosin IXa, but may contain amino acid substitutes, glycosylated residues or other chemical modifications.

"Fusions" or "chimeric polypeptides" are mutants, fragments, or the native CNGC-15 or Myosin IXa that also include amino and/or carboxyl terminal amino acid extensions. For example, Myosin Ixa fragments may be fused with fragments of other unconventional myosins. Unconventional myosins are members of the myosin superfamily that display the general head, neck and tail domain structure of conventional myosins (Mooseker et al. (1995) *Annu. Rev. Cell. Dev. Biol.* 11:633–75), but differ from conventional myosins by changes in these and/or the inclusion of additional functional domains. The head region shared among all myosin molecules consists of conserved amino acid sequences that span approximately 80 kDa while the neck region contains conserved motifs that bind one to six light chains of protein from the calmodulin/EF-hand family (Bahler et al. (1996) *Curr. Op. Cell. Biol.* 8:18–22). It is the unconventional myosin tail domains that show the most variation from conventional myosin and from each other. For example, although myosin Va has a coiled coil tail domain, as does conventional myosin, it also contains a PEST site (required for calpain cleavage) and a globular C-terminal domain which may be used for interactions with cargo or docking proteins. Myosin VIIa also has a coiled coil tail domain, however it contains additional domains different from those found in myosin Va, such as the talin domain which is thought to be active in binding plasma membranes. As a third example, the class IX myosins (composed of rat myr5 and human myosin IXb) have even less similart to conventional myosin and to the other nine classes of unconventional myosins. These molecules lack a coiled coil domain in the tail region, but do contain a GAP (GTP activating protein) domain which increases the GTPase activity of rhoA and Cdc42 (Reinhard et al. (1995) *EMBO J*. 14:697–704). Class IX myosins also have two large insertions in the conserved head domain that are absent in conventional and other unconventional myosins, and may act as regulatory domains affecting the mechanochemical properties of the protein. Despite the variation among these three examples of unconventional myosin classes, all classes bind actin and have either been shown to be or are postulated to act as molecular motors (Wang et al. (1996) *Science* 273:660–663), thereby interacting with the actin cytoskeleton. The characterization and chromosomal mapping of myosin Va and myosin VIIa suggested that these molecules may be responsible for specific human diseases. Indeed, defects in myosin Va are associated with Griscelli disease (Pastural et al. (1997) *Nature Genet*. 16:289–292), while mutations in myosin VIIa are responsible for Usher Sydrome type 1B (Weil et al. (1995) *Nature* 374:60–61.

The number or type of the amino acid substitutions is not critical, nor is the length or number of the amino acid deletions, or amino acid extensions that are incorporated in the CNGC-15 or Myosin IXa polypeptides. However, all of these polypeptides will exhibit at least about 20% of one of the activities of the native CNGC-15 or Myosin IXa. More typically, the polypeptides exhibit at least about 40%, even more typically the polypeptides exhibit at least about 60% of one of the native CNGC-15 or Myosin IXa activities. All these polypeptides will retain at least about 50% amino acid identity with SEQ ID NO: 1 or SEQ ID NO: 3; more typically, at least about 60%; even more typically, at least about 80%. Preferably, these polypeptides will retain at least about 85% amino acid sequence identity with SEQ ID NO: 1 or the amino acid sequence encoded by SEQ ID NO: 3; more preferably, at least about 90%; even more preferably, at least about 95%.

Myosin IXa activities include immunological activities, ATP binding, ATPase activity (Shyamata et al. (1990) J Cell Biol 110:1137–1147), zinc binding (Reinhard et al. (1995) EMBO J 14:697–704; Quest et . (1994) J Biol Chem 269:2961–2970) calmodulin/EF binding (Glenney et al. (1980) J Biol Chem 255:10551–10554; Cheney, (1992) Current Opin Cell Biol 4:27–35), binding to G-coupled receptors, GTPase activity (Reinhard, Supra; Ridley (1992) Cell 70:401–410), membrane binding (Reizes (1994) PNAS USA 91:6439–6443) phorbolester binding (Reinhard, Supra), modulation of cell to cell interactions, calcium release and cytoskeletal rearrangements, actin binding (Ruppert et al. (1993) J Cell Biol 120:1393–1403; Ridley et al. (1992) Cell 70:389–399; Ridley et al. (1992) Cell 70:401–410), formation of focal complexes (Ridley, Supra), synthesis of phosphatidylinositol-4,5-bis-phosphate, activation of transcription and DNA synthesis and transduction of chemical energy into mechanical force along actin filaments (Collins et al. (1990) J Cell Biol 110:1137–1147).

"Hybridization" refers to the association of two nucleic acid sequences to one another by hydrogen bonding. Factors that affect this bonding are discussed in Sambrook et al. (1989) *Molecular Cloning: A Laboratory Manual, Second Edition*, Volume 2, chapter 9, pages 9.47 to 9.57. A nucleic acid probe is said to "hybridize" with SEQ ID NO: 2 or SEQ ID NO: 3 if the probe can form a duplex or double stranded complex, which is stable enough to be detected. Hybridization of the probe to a polynucleotide of SEQ ID NO: 2 or SEQ ID NO: 3 depends on (1) the sequence of the nucleic acid probe and (2) the hybridization conditions. The sequence of the probe need not be exactly complementary. For example, a non-complementary nucleotide sequence may be attached to the 5' end of the probe, with the remainder of the probe sequence being complementary to SEQ ID NO: 2 or SEQ ID NO: 3. Alternatively, non-complementary bases or longer sequences can be interspersed into the probe, provided that the probe sequence has sufficient complementarity with SEQ ID NO: 2 or SEQ ID NO: 3 to hybridize therewith and thereby form a duplex which can be detected. The exact length and sequence of the probe will depend on the hybridization conditions, such as temperature, salt condition and the like. For example, for diagnostic applications, depending on the complexity of the analyte sequence, the nucleic acid probe typically contains 15–25 or more nucleotides, although it may contain fewer nucleotides. Short primers generally require cooler temperatures to form sufficiently stable hybrid complexes with the template.

Two sequences can be aligned using the methods and computer programs described above, and include BLAST, available over the world wide web at http://ww.ncbi.nlm.nih.gov/BLAST/. Another alignment algorithm is Fasta, available in the Genetics Computing Group (GCG) package, Madison, Wis., USA, a wholly owned subsidiary of Oxford Molecular Group, Inc. Other techniques for alignment are described in Doolittle, Methods in Enzymology, Supra. Preferably, an alignment program that permits gaps in the sequence is utilized to align the sequences. The Smith-Waterman is one type of algorithm that permits gaps in sequence alignments. See *Meth. Mol. Biol.* 70: 173–187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. EST-encoded amino acid sequences can be used to search both protein and DNA databases.

Of interest is the BestFit program using the local homology algorithm of Smith Waterman (Advances in Applied Mathematics 2: 482–289 (1981)) to determine sequence identity. The gap generation penalty will generally range from about 1 to about 5, usually, about 2 to about 4 and in many embodiments will be about 3. The gap extension penalty will generally range from about 0.01 to 0.20 and in many instances will be 0.10. The program has default parameters determined by the sequences inputted to be compared. Preferably, the sequence identity is determine used the parameters determined by the program. This program is available from Genetics Computing Group (GCG), Madison, Wis., USA.

Additional factors used to determine sequence identity are: percentage of the alignment region length where the strongest alignment is found, percent sequence identity, and p value.

The percentage of the alignment region length is calculated by counting the number of residues of the individual sequence found in the region of strongest alignment. This number is divided by the total residue length of the query sequence to find a percentage. An example is shown below:

Sequence A: ASNPERTMIPVTRVGLIRYM
         |  ||| ||
Sequence B: YMMTEYLAIPV.RVGLPRYM
         1    5   10 15

The region of alignment begins at amino acid 9 and ends at amino acid 19. The total length of the query sequence is 20 amino acids. The percent of the alignment region length is 11 divided by 20 or 55%.

Percent sequence identity is calculated by counting the number of amino acid matches between the two sequences and dividing total number of matches by the number of residues of the individual sequence found in the region of strongest alignment. For the example above, the percent identity would be 10 matches divided by 11 amino acids, or approximately, 90.9%

For the alignment results to be considered high similarity, the percent of the alignment region length, typically, is at least about 55% of total length one of the sequences; more typically, at least about 58%; even more typically; at least about 60% of the total residue length of one of the sequences. Usually, percent length of the alignment region can be as much as about 62%; more usually, as much as about 64%; even more usually, as much as about 66%. Typically, the percent length of alignment region is at least about 75% of the total length of one of the sequences; more typically, at least about 80%; even more typically, about 85%, about 90%, about 95%, about 98%, or 99%.

P value is the probability that the alignment was produced by chance. For a single alignment, the p value can be calculated according to Karlin et al., *Proc. Natl. Acad. Sci.* 87: 2264 (1990) and Karlin et al., *Proc. Natl. Acad. Sci.* 90: (1993). The p value of multiple alignments using the same query sequence can be calculated using an heuristic approach described in Altschul et al., *Nat. Genet.* 6: 119 (1994). Alignment programs such as BLAST program can calculate the p value.

The two sequences, typically, exhibit a p value is less than or equal to about $10^{-2}$; more usually; less than or equal to about $10^{-3}$; even more usually; less than or equal to about $10^{-4}$. More typically, the p value is no more than about $10^{-5}$; more typically; no more than or equal to about $10^{-10}$; even more typically; no more than or equal to about $10^{-15}$. Preferably, the p value is no more than about $10^{-20}$; more preferably, no more than about $10^{-30}$; even more preferably, no more than about $10^{-40}$, about $10^{-50}$, or $10^{-60}$.

The boundaries of the region where the sequences align can be determined according to Doolittle, Methods in Enzymology, Supra; BLAST or FAST programs; or by determining the area where the sequence identity is highest.

Another factor to consider for determining identity or similarity is the location of the similarity or identity. Strong local alignment can indicate similarity even if the length of alignment is short. Sequence identity scattered throughout the length of the one sequence also can indicate a similarity between two sequences.

"Stringency" refers to conditions in a hybridization reaction that favor association of very similar sequences over sequences that differ. Factors affecting the stringency of hybridization are well known to those skilled in the art and are discussed in Sambrook et al. above at page 9.50.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If nonspecific bands or high background are observed after autoradiography, the filter can be washed at high stringency and reexposed. If the time required for exposure makes this approach impractical, several hybridization and/or washing stringencies should be tested in parallel.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

A composition containing A is "substantially free of" B when at least about 85% by weight of the total A+B in the composition is A. Preferably, A comprises at least about 90% by weight of the total of A+B in the composition, more preferably at least about 95% or even 99% by weight.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Heterologous components may be from the same or different organisms. Another example is where a human CNGC-15 or Myosin IXa coding sequence is heterologous to a mouse host cell.

A "promoter" is a DNA sequence that initiates and regulates the transcription of a coding sequence when the promoter is operably linked to the coding sequence. A promoter is "heterologous" to the coding sequence when the promoter is not operably linked to the coding sequence in nature. For example, a human CNGC-15 Myosin IXa promoter would comprise an expression cassette wherein a nucleotide sequence encoding CNGC-15 is operably linked to a heterologous promoter. A "native" promoter is operably linked to the coding sequence in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. With certain origins of replication, an expression vector can be reproduced at a high copy number in the presence of the appropriate proteins within the cell. Examples of origins are the $2\mu$ and autonomously replicating sequences, which are effective in yeast; and the viral T-antigen, effective in COS-7 cells.

Host cells capable of producing CNGC-15 and/or Myosin IXa polypeptides are cultured "under conditions allowing expression." Such conditions allow transcription and translation of the DNA molecule encoding the CNGC-15 and/or Myosin IXa polypeptide. These conditions include cultivation temperature, oxygen concentration, media composition, pH, etc. For example, if the trp promoter is utilized in the expression vector, the media will lack tryptophan to trigger the promoter and induce expression. The exact conditions will vary from host cell to host cell and from expression vector to expression vector.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, altered antibodies, univalent antibodies, the Fab proteins, and single domain antibodies.

"Myosin IXa-modulated disorders" and "CNGC-15 modulated-disorders" include, but are not limited to Bardet-Biedl Syndrome, Usher Syndrome, hearing loss, retinis pigmentosa, obesity, hypogonadism, sterility, polydactyly, brachydactyly, syndactyly, mental retardation, renal abnormalities, hypertension, diabetes and cardiovascular abnormalities B. General Method This invention provides the amino acid and nucleotide sequences of CNGC-15 and Myosin IXa. With these disclosed sequences, nucleic acid probe assays and expression cassettes and vectors for CNGC-15 and Myosin IXa polypeptides can be produced. The expression vectors can be transformed into host cells to produce CNGC-15 and/or Myosin IXa polypeptides. The purified polypeptides can be used to produce antibodies to detect CNGC-15 or Myosin IXa. Also, the host cells or extracts can be utilized for biological assays to isolate agonists or antagonists.

Nucleic Acid CNGC-15 Probe Assays mRNA levels in different cell types can be detected with nucleic acid probe assays. For example, PCR, branched DNA probe assays, or blotting techniques utilizing nucleic acid probes substantially identical or complementary to SEQ ID NO: 2 or SEQ ID NO: 3 can determine the presence of CNGC-15 or Myosin IXa cDNA or mRNA.

For genomic analysis or detection of denatured DNA, the nucleic acid probes will hybridize to a nucleotide sequence encoding the amino acid sequence shown in SEQ ID NO: 1 or encoded by SEQ ID NO: 3, or the complement of a sequence encoding SEQ ID NO: 1 or the polypeptide encoded by SEQ ID NO: 3. Though many different nucleotide sequences will encode the amino acid sequences, SEQ ID NO: 2 and SEQ ID NO: 3 are preferred because they are the actual sequences present in human cells. For single-stranded cDNA detection, the nucleic acid probe will hybridize to the complement of a nucleotide sequence encoding the amino acid sequence of SEQ ID NO: 1 or encoding the polypeptide encoded by nucleotides 369–1307 of SEQ ID NO: 3 or to a complement of SEQ ID NO: 2 or SEQ ID NO: 3. For mRNA detection, the nucleic acid probe will hybridize to SEQ ID NO: 2 or SEQ ID NO: 3 or to a nucleotide sequence encoding the amino acid sequence of SEQ ID NO: 1 or encoding the polypeptide encoded by SEQ ID NO: 3. The nucleic acid probe sequences need not be identical to SEQ ID NO: 2, SEQ ID NO: 3 or their complement.

Probes are typically at least about 20 nucleotides, more preferably at least about 30 nucleotides. The probes may be produced by synthetic procedures, such as the triester method of Matteucci et al. (1981) *J. Am. Chem. Soc.* 103:3185, or according to Urdea et al. (1983) *Proc. Natl. Acad. Sci. USA* 80:7461, or using commercially available automated oligonucleotide synthesizers. One example of a nucleotide hybridization assay is described in Urdea et al. PCT WO92/02526 and Urdea et al. U.S. Pat. No. 5,124,246, herein incorporated by reference. Other methods of hybridization and detection are known to those skilled in the art.

Alternatively, the Polymerase Chain Reaction (PCR) is another well-known means for detecting small amounts of target nucleic acids. The assay is described in Mullis et al. (1987) *Meth. Enzymol.* 155:335–350; U.S. Pat. No. 4,683,195; and U.S. Pat. No. 4,683,202, incorporated herein by reference. Also, mRNA, cDNA and genomic DNA can be detected by traditional blotting techniques described in Sambrook et al. (1989) *Molecular Cloning: A Laboratory Manual* (New York, Cold Spring Harbor Laboratory).

Expression of CNGC-15 and Myosin IXa Polypeptides

Preferably, CNGC-15 and Myosin IXa polypeptides are produced by recombinantly engineered host cells. These host cells are constructed by the introduction of a expression vector comprising a promoter operably linked to a CNGC-15 or Myosin IXa polypeptide coding sequence.

Such coding sequences can be constructed by synthesizing the entire gene or by altering existing CNGC-15 or Myosin IXa polypeptide coding sequences. CNGC-15 and Myosin IXa polypeptides can be divided into four general categories: mutants, fragments, fusions, and the native CNGC-15 or Myosin IXa polypeptides. The CNGC-15 polypeptides are those that occur in nature. The amino acid sequence of such polypeptides may vary slightly from SEQ ID NO: 1. The native CNGC-15 and Myosin IXa polypeptide coding sequence can be selected based on the amino acid sequence shown in SEQ ID NO: 1 or the amino acid sequence predicted by the open reading frame of SEQ ID NO: 3. For example, synthetic genes can be made using codons preferred by the host cell to encode the desired polypeptide. (See Urdea et al. (1983) *Proc. Natl. Acad. Sci. USA* 80:7461). Alternatively, the desired native CNGC-15 and Myosin IXa polypeptide coding sequences can be cloned from nucleic acid libraries. Techniques for producing and probing nucleic acid sequence libraries are described, for example, in Sambrook et al. (1989) *Molecular Cloning: A Laboratory Manual* (New York, Cold Spring Harbor Laboratory). Other recombinant techniques, such as site specific mutagenesis, PCR, enzymatic digestion and ligation, can also be used to construct the desired CNGC-15 polypeptide coding sequence.

The native CNGC-15 and Myosin IXa polypeptide coding sequences can be modified to create the other classes of CNGC-15 and Myosin IXa polypeptides. For example, mutants can be created by making conservative amino acid substitutions that maintain or enhance native CNGC-15 or Myosin IXa activity. The following are examples of conservative substitutions: Gly⇔Ala; Val⇔Ile⇔Leu; Asp⇔Glu; Lys⇔Arg; Asn⇔Gln; and Phe⇔Trp⇔Tyr. Mutants can also contain amino acid deletions or insertions compared to the native CNGC-15 or Myosin IXa polypeptides. Mutants may include substitutions, insertions, and deletions of the native polypeptides.

Mutants will retain at least about 20% of the one of the activities of the native CNGC-15 or Myosin IXa. The coding sequence of mutants can be constructed by in vitro mutagenesis of the native coding sequences.

A subset of mutants is a group of polypeptides with the non-disulfide bond participating cysteines substituted with a neutral amino acid, generally, with serines. These mutants may be stable over a broader temperature range than native CNGC-15 or Myosin IXa polypeptides. See, for example, Mark et al., U.S. Pat. No. 4,959,314.

Fragments differ from mutant or native CNGC-15 or Myosin IXa polypeptides by amino and/or carboxyl terminal amino acid deletions. The number of amino acids that are truncated is not critical as long as the CNGC-15 or Myosin IXa fragment retains at least about 20% of the one of the activities of the native CNGC-15 or Myosin IXa polypeptide. The coding sequence of such fragments can be easily constructed by cleaving the unwanted nucleotides from the mutant or native CNGC-15 or Myosin IXa polypeptide coding sequences.

Fusions are fragment, mutant, or native CNGC-15 or Myosin IXa polypeptides with additional amino acids at either or both of the termini. The additional amino acid sequence is not necessarily homologous to sequence found in native polypeptides. The fusions, just as all CNGC-15 and Myosin IXa polypeptides, retain at least about 20% of one of the activities of the native CNGC-15 or Myosin IXa polypeptides. Coding sequence of the fusions can be constructed by ligating synthetic polynucleotides encoding the additional amino acids to fragment, mutant, or native coding sequences. Activities of the CNGC-15 and Myosin IXa polypeptides can be determined by the methods described infra.

Expression Vectors

At the minimum, an expression vector will contain a promoter which is operable in the host cell and operably linked to a CNGC-15 or Myosin IXa coding sequence. Sequences that modulate gene expression, such as enhancers and binding sites for inducers or repressors may be present. Expression vectors may also include signal sequences, terminators, selectable markers, origins of replication, and sequences homologous to host cell sequences. These additional elements are optional but can be included to optimize expression.

Functional non-natural promoters may also be used, for example, synthetic promoters based on a consensus sequence of different promoters. Also, effective promoters can contain a regulatory region linked with a heterologous expression initiation region. Examples of hybrid promoters are the *E. coli* lac operator linked to the *E. coli* tac transcription activation region; the yeast alcohol dehydrogenase (ADH) regulatory sequence linked to the yeast glyceraldehyde-3-phosphate-dehydrogenase (GAPDH) transcription activation region (U.S. Pat. Nos. 4,876,197 and 4,880,734, incorporated herein by reference); and the cytomegalovirus (CMV) enhancer linked to the SV40 (simian virus) promoter.

A CNGC-15 or Myosin IXa polypeptide coding sequence may also be linked in reading frame to a signal sequence. The signal sequence fragment typically encodes a peptide comprised of hydrophobic amino acids which directs the CNGC-15 or Myosin IXa polypeptide to the cell membrane or other subcellular compartment. Preferably, there are processing sites encoded between the leader fragment and the gene or fragment thereof that can be cleaved either in vivo or in vitro. DNA encoding suitable signal sequences can be derived from genes for secreted endogenous host cell proteins, such as the yeast invertase gene (EP 12 873; JP 62,096,086), the A-factor gene (U.S. Pat. No. 4,588,684), interferon signal sequence (EP 60 057).

A preferred class of secretion leaders, for yeast expression, are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (typically about 25 to about 50 amino acid residues) (U.S. Pat. Nos. 4,546,083 and 4,870,008, incorporated herein by reference; EP 324 274). Additional leaders employing an alpha-factor leader fragment that provides for secretion include hybrid alpha-factor leaders made with a presequence of a first yeast signal sequence, but a pro-region from a second yeast alpha-factor. (See e.g., PCT WO 89/02463).

Typically, terminators are regulatory sequences, such as polyadenylation and transcription termination sequences, located 3' or downstream of the stop codon of the coding sequences. Usually, the terminator of native host cell proteins are operable when attached 3' of a CNGC-15 or Myosin IXa polypeptide coding sequences. Examples are the *Saccharomyces cerevisiae* alpha-factor terminator and the baculovirus terminator. Further, viral terminators are also operable in certain host cells; for instance, the SV40 terminator is functional in CHO cells.

For convenience, selectable markers, an origin of replication, and homologous host cells sequences may optionally be included in an expression vector. A selectable marker can be used to screen for host cells that potentially contain the expression vector. Such markers may render the host cell immune to drugs such as ampicillin, chloramphenicol, erythromycin, neomycin, and tetracycline. Also, markers may be biosynthetic genes, such as those in the histidine, tryptophan, and leucine pathways. Thus, when leucine is absent from the media, for example, only the cells with a biosynthetic gene in the leucine pathway will survive.

An origin of replication may be needed for the expression vector to replicate in the host cell. Certain origins of replication enable an expression vector to be reproduced at a high copy number in the presence of the appropriate proteins within the cell. Examples of origins are the $2\mu$ and autonomously replicating sequences, which are effective in yeast; and the viral T-antigen, effective in COS-7 cells.

Expression vectors may be integrated into the host cell genome or remain autonomous within the cell. Polynucleotide sequences homologous to sequences within the host cell genome may be needed to integrate the expression cassette. The homologous sequences do not always need to be linked to the expression vector to be effective. For example, expression vectors can integrate into the CHO genome via an unattached dihydrofolate reductase gene. In yeast, it is more advantageous if the homologous sequences flank the expression cassette. Particularly useful homologous yeast genome sequences are those disclosed in PCT WO 90/01800, and the HIS4 gene sequences, described in Genbank, Accession No. J01331.

The choice of promoter, terminator, and other optional elements of an expression vector will also depend on the host cell chosen. The invention is not dependent on the host cell selected. Convenience and the level of protein expression will dictate the optimal host cell. A variety of hosts for expression are known in the art and available from the American Type Culture Collection (ATCC). Bacterial hosts suitable for expressing a CNGC-15 and/or Myosin IXa polypeptide include, without limitation: Campylobacter, Bacillus, Escherichia, Lactobacillus, Pseudomonas, Staphylococcus, and Streptococcus. Yeast hosts from the following genera may be utilized: Candida, Hansenula, Kluyveromyces, Pichia, Saccharomyces, Schizosaccharomyces, and Yarrowia. Immortalized mammalian host cells include but are not limited to CHO cells, HeLa cells, baby hamster kidney (BHK) cells, monkey kidney cells (COS), human hepatocellular carcinoma cells (e.g., Hep G2), and other cell lines. A number of insect cell hosts are also available for expression of heterologous proteins: *Aedes aegypti, Bombyx mori, Drosophila melanogaster*, and *Spodopterafrugiperda* (PCT WO 89/046699; Carbonell et al. (1985) *J. Virol.* 56:153; Wright et al. (1986) *Nature* 321:718; Smith et al. (1983) *Mol. Cell. Biol.* 3:2156; and see generally, Fraser et al. (1989) *In Vitro Cell. Dev. Biol.* 25:225).

Transformation

After vector construction, the desired CNGC-15 and/or Myosin IXa polypeptide expression vector is inserted into the host cell. Many transformation techniques exist for inserting expression vectors into bacterial, yeast, insect, and mammalian cells. The transformation procedure to introduce the expression vector depends upon the host to be transformed.

Methods of introducing exogenous DNA into bacterial hosts are well-known in the art, and typically protocol includes either treating the bacteria with $CaCl_2$ or other agents, such as divalent cations and DMSO. DNA can also be introduced into bacterial cells by electroporation or viral infection. Transformation procedures usually vary with the bacterial species to be transformed. See e.g. (Masson et al. (1989) *FEMS Microbiol. Lett.* 60:273; Palva et al. (1982) *Proc. Natl. Acad. Sci. USA* 79:5582; EP Publ. Nos. 036 259 and 063 953; PCT WO 84/04541, Bacillus), (Miller et al. (1988) *Proc. Natl. Acad. Sci.* 85:856; Wang et al. (1990) *J. Bacteriol.* 172:949, Campylobacter), (Cohen et al. (1973) *Proc. Natl. Acad. Sci.* 69:2110; Dower et al. (1988) *Nucleic Acids Res.* 16:6127; Kushner et al. (1978) "An Improved Method for Transformation of *Escherichia coli* with ColE1-derived plasmids in *Genetic Engineering: Proceedings of the International Symposium on Genetic Engineering* (eds. H. W. Boyer and S. Nicosia); Mandel et al. (1970) *J. Mol. Biol.* 53:159; Taketo et al. (1988) *Biochim. Biophys. Acta* 949:318; Escherichia), (Chassy et al. (1987) *FEMS Microbiol. Lett.* 44:173, Lactobacillus); (Fiedler et al. (1988) *Anal. Biochem.* 170:38, Pseudomonas); (Augustin et al. (1990) *FEMS Microbiol. Lett.* 66:203, Staphylococcus), Barany et al. (1980) *J. Bacteriol.* 144:698; Harlander et al. (1987) "Transformation of *Streptococcus lactis* by electroporation," in *Streptococcal Genetics* (ed. J. Ferretti and R. Curtiss, III); Perry et al. (1981) *Infec. Immun.* 32:1295; Powell et al. (1988) *Appl. Environ. Microbiol.* 54:655; Somkuti et al. (1987) *Proc. 4th Evr. Cong. Biotechnology* 1:412, Streptococcus).

Transformation methods for yeast hosts are well-known in the art, and typically include either the transformation of spheroplasts or of intact yeast cells treated with alkali cations. Electroporation is another means for transforming yeast hosts. See for example, *Methods in Enzymology*, Volume 194, 1991, "Guide to Yeast Genetics and Molecular Biology." Transformation procedures usually vary with the yeast species to be transformed. See e.g. (Kurtz et al. (1986) *Mol. Cell. Biol.* 6:142; Kunze et al. (1985) *J. Basic Microbiol.* 25:141, Candida); (Gleeson et al. (1986) *J. Gen. Microbiol.* 132:3459; Roggenkamp et al. (1986) *Mol. Gen. Genet.* 202:302, Hansenula); (Das et al. (1984) *J. Bacteriol.* 158:1165; De Louvencourt et al. (1983) *J. Bacteriol.* 154:1165; Van den Berg et al. (1990) *Biotechnology* 8:135, Kluyveromyces); (Cregg et al. (1985) *Mol. Cell. Biol.* 5:3376; Kunze et al. (1985) *J. Basic Microbiol.* 25:141; U.S. Pat. Nos. 4,837,148 and 4,929,955, Pichia); (Hinnen et al. (1978) *Proc. Natl. Acad. Sci. USA* 75:1929; Ito et al. (1983)

J. Bacteriol. 153:163, Saccharomyces); (Beach and Nurse (1981) Nature 300:706, Schizosaccharomyces); (Davidow et al. (1985) Curr. Genet. 10:39; Gaillardin et al. (1985) Curr. Genet. 10:49, Yarrowia).

Methods for introducing heterologous polynucleotides into mammalian cells are known in the art and include viral infection, dextran-mediated transfection, calcium phosphate precipitation, microparticle bombardment, protoplast fusion, electroporation, encapsulation of the polynucleotide(s) in liposomes, and direct microinjection of the DNA into nuclei.

The method for construction of an expression vector for transformation of insect cells for expression of recombinant herein is slightly different than that generally applicable to the construction of a bacterial expression vector, a yeast expression vector, or a mammalian expression vector. In an embodiment of the present invention, a baculovirus vector is constructed in accordance with techniques that are known in the art, for example, as described in Kitts et al. (1993) Biotechniques 14:810–817; Smith et al. (1983) Mol. Cell. Biol. 3:2156; and Luckow and Summer (1989) Virol. 17:31. In one embodiment of the present invention, a baculovirus expression vector is constructed substantially in accordance to Summers and Smith, Texas Agricultural Experiment Station Bulletin No.1555 (1987). Moreover, materials and methods for baculovirus/insect cell expression systems are commercially available in kit form, for example, the Max-Bac kit from Invitrogen (San Diego, Calif.).

Also, methods for introducing heterologous DNA into an insect host cell are known in the art. For example, an insect cell can be infected with a virus containing a CNGC-15 or Myosin IXa polypeptide coding sequence. When the virus is replicating in the infected cell, the CNGC-15 or Myosin IXa polypeptide will be expressed if operably linked to a suitable promoter. A variety of suitable insect cells and viruses are known and include following without limitation.

Insect cells from any order of the Class Insecta can be used to express the polypeptide of this invention. The orders Diptera and Lepidoptera are preferred. Example of insect species are listed in Weiss et al. "Cell Culture Methods for Large-Scale Propagation of Baculoviruses," in Granados et al. (eds., The Biology ofBaculoviruses: Vol. II Practical Application for Insect Control, pp. 63–87 at p. 64 (1987). Insect cell lines derived from the following insects are exemplary: Carpocapsa pomeonella (preferably, cell line CP-128); Trichoplusia ni (preferably, cell line TN-368); Autograph californica; Spodoptera frugiperda (preferably, cell line Sf9); Lymantria dispar; Mamestra brassicae; Aedes albopictus; Orgyia pseudotsugata; Neodiprio sertifer; Aedes aegypti; Antherae eucalypti; Gnorimoschema operceullela; Galleria mellonella; Spodoptera littolaris; Blatella germanic; Drosophila melanogaster; Heliothis zea; Spodoptera exigua; Rachiplusia ou; Plodia interpunctella; Amsaeta moorei; Agrotis c-nigrum, Adoxophyes orana; Agrotis segetum; Bombyx mori; Hyponomeuta malinellu; Colias eurytheme; Anticarsia germmetalia; Apanteles melanoscelu; Arctia caja; and Porthetria dispar. Preferred insect cell lines are from Spodoptera frugiperda, and especially preferred is cell line Sf9. The Sf9 cell line used in the examples herein was obtained from Max D. Summers (Texas A & M University, College Station, Tex., 77843, USA). Other S. frugiperda cell lines, such as IPL-Sf-21AE III, are described in Vaughn et al. (1977) In Vitro 13:213–217.

The insect cell lines of this invention are suitable for the reproduction of numerous insect-pathogenic viruses such as parvoviruses, pox viruses, baculoviruses and rhabdoviruses, of which nucleopolyhedrosis viruses (NPV) and granulosis viruses (GV) from the group of baculoviruses are preferred. Further preferred are NPV viruses such as those from Autographa spp., Spodoptera spp., Trichoplusia spp., Rachiplusia spp., Gallerai spp., and Lymantria spp. More preferred are baculovirus strain Autographa californica NPV (AcNPV), Rachiplusia ou NPV, Galleria mellonella NPV, and any plaque purified strains of AcNPV, such as E2, R9, S1, M3, characterized and described by Smith et al. (1978) Virol. 89:517–527.

Typically, insect cells Spodoptera frugiperda type 9 (SF9) are infected with baculovirus strain Autographa californica NPV (AcNPV) containing a CNGC-15 or Myosin IXa polypeptide coding sequence. Such a baculovirus is produced by homologous recombination between a transfer vector containing the coding sequence and baculovirus sequences and a genomic baculovirus DNA. Preferably, the genomic baculovirus DNA is linearized and contains a dysfinctional essential gene. The transfer vector, preferably, contains the nucleotide sequences needed to restore the dysfunctional gene and a baculovirus polyhedrin promoter and terminator operably linked to the CNGC-15 or Myosin IXa coding sequence. (See Kitts et al. (1993) Biotechniques 14(5):810–817.

The transfer vector and linearized baculovirus genome are transfected into SF9 insect cells, and the resulting viruses probably containing the desired coding sequence. Without a functional essential gene the baculovirus genome cannot produce a viable virus. Thus, the viable viruses from the transfection most likely contain the CNGC-15 or Myosin IXa polypeptide coding sequence and the needed essential gene sequences from the transfer vector. Further, lack of occlusion bodies in the infected cells are another verification that the CNGC-15 or Myosin IXa polypeptide coding sequence was incorporated into the baculovirus genome.

The essential gene and the polyhedrin gene flank each other in the baculovirus genome. The coding sequence in the transfer vector is flanked at its 5' with the essential gene sequences and the polyhedrin promoter and at its 3' with the polyhedrin terminator. Thus, when the desired recombination event occurs the CNGC-15 or Myosin IXa polypeptide coding sequence displaces the baculovirus polyhedrin gene. Such baculoviruses without a polyhedrin gene will not produce occlusion bodies in the infected cells. Of course, another means for determining if coding sequence was incorporated into the baculovirus genome is to sequence the recombinant baculovirus genomic DNA. Alternatively, expression of the desired CNGC-15 or Myosin IXa polypeptide by cells infected with the recombinant baculovirus is another verification means.

Monitoring CNGC-15 Polypeptide Expression Levels

Immunoassays and ligand binding assays can be utilized to confirm that the transformed host cell is expressing the desired CNGC-15 and/or Myosin IXa polypeptide.

For example, an immunofluorescence assay can be performed on transformed host cells without separating the CNGC-15 or Myosin IXa polypeptides from the cell. The host cells are first fixed onto a solid support, such as a microscope slide or microtiter well. This fixing step permeabilizes the cell membrane. Next, the fixed host cells are exposed to an anti-CNGC-15 or anti-Myosin IXa polypeptide antibody. Preferably, to increase the sensitivity of the assay, the fixed cells are exposed to a second antibody, which is labeled and binds to the anti-CNGC-15 or anti-Myosin IXa polypeptide antibody. Typically, the secondary antibody is labeled with an fluorescent marker. The host cells which express the CNGC-15 or Myosin IXa polypeptides will be fluorescently labeled and easily visualized under the microscope. See, for example, Hashido et al. (1992) *Biochem & Biophys. Res. Comm.* 187(3):1241–1248.

Also, the CNGC-15 and Myosin IXa polypeptides do not need to be separated from the cell membrane for in vitro assays. The host cells may be fixed to a solid support, such as a microtiter plate. Alternatively, a crude membrane fraction can be separated from lysed host cells by centrifugation (See Adachi et al. (1992) *FEBS Lett* 311 (2):179–183. The fixed host cells or the crude membrane fraction is exposed to labeled ligand or ion. Typically, the ligand is labeled with radioactive atoms. The host cells which express the desired CNGC-15 or Myosin IXa polypeptide will bind with the labeled ligand which can be easily detected.

Purification

The purified CNGC-15 and Myosin IXa polypeptides are useful as compositions, for assays, and to produce antibodies.

CNGC-15 and Myosin IXa polypeptides can be isolated by a variety of steps including, for example, anion exchange chromatography, size exclusion chromatography, hydroxyapatite chromatography, hydrophobic interaction chromatography, metal chelation chromatography, reverse phase HPLC, affinity chromatography, and further ammonium sulfate precipitations. These techniques are well known to those of skill in the art.

For ligand binding studies, patch clamp analysis or other in vitro assays, the crude cell membrane fractions can be utilized. These membrane extracts can be isolated from cells which expressed CNGC-15 or Myosin IXa polypeptides by lysing the cells. Alternatively, whole cells, expressing CNGC-15 and/or Myosin IXa polypeptides, can be cultured in a microtiter plate.

Antibodies

Antibodies against CNGC-15 and Myosin IXa polypeptides are useful for affinity chromatography, immunofluorescent assays, and distinguishing CNGC-15 and Myosin IXa polypeptides.

Antibodies to the proteins of the invention, both polyclonal and monoclonal, may be prepared by conventional methods known to those skilled in the art. For example, monoclonal antibodies are prepared using the method of Kohler et al. (1975) *Nature* 256:495–496, or a modification thereof.

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetra-methylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the instant invention.

Screening for Agonists and Antagonists

CNGC-15 and Myosin IXa polypeptides can also be used to screen combinatorial libraries to identify agonist or antagonists. For example, a "library" of peptides may be synthesized following the methods disclosed in U.S. Pat. No. 5,010,175, and in PCT WO 91/17823, both incorporated herein by reference in full. The peptide library is first screened for binding to the selected CNGC-15 or Myosin IXa polypeptide. The peptides are then tested for their ability to inhibit or enhance CNGC-15 or Myosin IXa activity. Peptides exhibiting the desired activity are then isolated and sequenced.

CNGC-15 and Myosin IXa agonists or antagonists may be screened using any available method. The assay conditions ideally should resemble the conditions under which the CNGC-15 or Myosin IXa activity is exhibited in vivo, i.e., under physiologic pH, temperature, ionic strength, etc. Suitable agonists or antagonists will exhibit strong inhibition or enhancement of the CNGC-15 or Myosin IXa activity at concentrations which do not raise toxic side effects in the subject. Agonists or antagonists which compete for binding to the CNGC-15 or Myosin IXa polypeptide may require concentrations equal to or greater than the native CNGC-15 or Myosin IXa concentration, while inhibitors capable of binding irreversibly to the polypeptide may be added in concentrations on the order of the native CNGC-15 or Myosin IXa concentration.

Signal Transduction Assays

Most cellular $Ca^{2+}$ ions are sequestered in the mitochondria, endoplasmic reticulum, and other cytoplasmic vesicles, but binding of endothelin to receptor will trigger the increase of free $Ca^{2+}$ ions in the cytoplasm. With fluorescent dyes, such asfura-2, the concentration of free $Ca^{2+}$ can be monitored. The ester of fura-2 is added to the media of the host cells expressing receptor polypeptides. The ester of fura-2 is lipophilic and diffuses across the membrane. Once inside the cell, the fura-2 ester is hydrolyzed by cytosolic esterases to its non-lipophilic form, and then the dye cannot diffuse back out of the cell. The non-lipophilic form of fura-2 will fluoresce when it binds to the free $Ca^{2+}$ ions, which are released after binding of a ligand to the receptor. The fluorescence can be measured without lysing the cells at an excitation spectrum of 340 nm and at fluorescence spectrum of 500 nm. See Sakurai et al. EP 480 381 and Adachi et al. (1992) *FEBS Lett* 311(2) :179–183 for examples of assays measuring free intracellular $Ca^{2+}$ concentrations.

The rise of free cytosolic $Ca^{2+}$ concentrations is preceded by the hydrolysis of phosphatidylinositol 4,5-bisphosphate. Hydrolysis of this phospholipid by the plasma-membrane enzyme phospholipase C yields 1,2-diacylglycerol (DAG), which remains in the membrane, and the water-soluble inositol 1,4,5-trisphosphate ($IP_3$). Binding of endothelin or endothelin agonists will increase the concentration of DAG and $IP_3$. Thus, signal transduction activity can be measured by monitoring the concentration of these hydrolysis products.

To measure the $IP_3$ concentrations, radioactively labeled $^3H$-inositol is added to the media of host cells expressing CNGC-15 or Myosin IXa polypeptides. The $^3H$-inositol taken up by the cells and after stimulation of the cells with endothelin or endothelin agonist, the resulting inositol triphosphate is separated from the mono and di-phosphate forms and measured. See Sakurai et al., EP 480 381. Alternatively, Amersham provides an inosital 1,4,5-trisphosphate assay system. With this system Amersham provides tritylated inosital 1,4,5-trisphosphate and a receptor capable of distinguishing the radioactive inositol from other inositol phosphates. With these reagents an effective and accurate competition assay can be performed to determine the inositol triphosphate levels.

Pharmaceutical Compositions

Pharmaceutical compositions can comprise either polypeptides, antibodies, or polynucleotides of the claimed invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician.

For purposes of the present invention, an effective dose will be from about 0.01 mg/kg to 50 mg/kg or 0.05 mg/kg to about 10 mg/kg of the polypeptide or DNA construct in the individual to which it is administered A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be mammals or birds. In particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a tumor or lesion. Other modes of administration include oral and pulmonary administration, suppositories, and transdermal applications, needles, and gene guns or hyposprays. Dosage treatment may be a single dose schedule or a multiple dose schedule.

Alternatively, the Myosin IXa or CNGC-15 polypeptides could be stably expressed in an organ of a mammal, and then the organ could be xenografted into a human in need of such treatment.

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector. See generally, Jolly et al. (1994) *Cancer Gene Therapy* 1:51–64; Kimura et al. (1994) *Human Gene Therapy* 5:845–852; Connelly et al. (1995) *Human Gene Therapy* 6:185–193; and Kaplitt et al. (1994) *Nature Genetics* 6:148–153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill (1985) *J. Vir.* 53:160) polytropic retroviruses (for example, MCF and MCF-MLV (see Kelly et al. (1983) *J. Vir.* 45:291), spumaviruses and lentiviruses. See RNA *Tumor Viruses*, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Ser. No. 07/800,921, filed Nov. 29, 1991). Retrovirus vectors can be constructed for site-specific integration into host cell DNA by incorporation of a chimeric integrase enzyme into the retroviral particle. See, U.S. Ser. No. 08/445,466 filed May 22, 1995. It is preferable but not required that the recombinant viral vector is a replication defective recombinant virus.

Packaging cell lines suitable for use with the above-described retrovirus vectors are well known in the art, are readily prepared (see U.S. Ser. No. 08/240,030, filed May 9, 1994; see also WO 92/05266), and can be used to create producer cell lines (also termed vector cell lines or "VCLs")

for the production of recombinant vector particles. Preferably, the packaging cell lines are made from human parent cells (e.g., HT1080 cells) or mink parent cell lines, which eliminates inactivation in human serum.

Preferred retroviruses for the construction of retroviral gene therapy vectors include Avian Leukosis Virus, Bovine Leukemia, Virus, Murine Leukemia Virus, Mink-Cell Focus-Inducing Virus, Murine Sarcoma Virus, Reticuloendotheliosis Virus and Rous Sarcoma Virus. Particularly preferred Murine Leukemia Viruses include 4070A and 1504A (Hartley et al. (1976) *J. Virol.* 19:19–25), Abelson (ATCC No. VR-999), Friend (ATCC No. VR-245), Graffi, Gross (ATCC Nol VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in Rockville, Md. or isolated from known sources using commonly available techniques.

Exemplary known retroviral gene therapy vectors employable in this invention include those described in GB 2200651, EP 0415731, EP 0345242, WO 89/02468, WO 89/05349, WO 89/09271, WO 90/02806, WO 90/07936, WO 94/03622, WO 93/25698, WO 93/25234, WO 93/11230, WO 93/10218, WO 91/02805, in U.S. Pat. No. 5,219,740, U.S. Pat. No. 4,405,712, U.S. Pat. No. 4,861,719, U.S. Pat. No. 4,980,289 and U.S. Pat. No. 4,777,127, in U.S. Ser. No. 07/800,921 and in Vile et al. (1993) *Cancer Res.* 53:3860–3864; Vile et al. (1993) *Cancer Res.* 53:962–967; Ram et al. (1993) *Cancer Res.* 53:83–88; Takamiya et al. (1992) *J. Neurosci. Res.* 33:493–503; Baba et al. (1993) *J. Neurosurg.* 79:729–735; Mann et al. (1983) *Cell* 33:153; Cane et al. (1984) *Proc. Natl. Acad. Sci.* 81:6349; and Miller et al. (1990) *Human Gene Therapy* 1.

Human adenoviral gene therapy vectors are also known in the art and employable in this invention. See, for example, Berkner et al. (1988) *Biotechniques* 6:616; Rosenfeld et al. (1991) *Science* 252:431; and WO 93/07283, WO 93/06223, and WO 93/07282. Exemplary known adenoviral gene therapy vectors employable in this invention include those described in the above referenced documents and in WO 94/12649, WO 93/03769, WO 93/19191, WO 94/28938, WO 95/11984, WO 95/00655, WO 95/27071, WO 95/29993, WO 95/34671, WO 96/05320, WO 94/08026, WO 94/11506, WO 93/06223, WO 94/24299, WO 95/14102, WO 95/24297, WO 95/02697, WO 94/28152, WO 94/24299, WO 95/09241, WO 95/25807, WO 95/05835, WO 94/18922, WO 95/09654. Alternatively, administration of DNA linked to killed adenovirus as described in Curiel et al. (1992) *Hum. Gene Ther.* 3:147–154 may be employed.

The gene delivery vehicles of the invention also include adenovirus associated virus (AAV) vectors. Leading and preferred examples of such vectors for use in this invention are the AAV-2 based vectors disclosed in Srivastava, WO 93/09239. Most preferred AAV vectors comprise the two AAV inverted terminal repeats in which the native D-sequences are modified by substitution of nucleotides, such that at least about 5 native nucleotides and up to 18 native nucleotides, preferably at least about 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (i.e., there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini et al. (1993) *Gene* 124:257–262. Another example of such an AAV vector is psub201. See Samulski et al. (1987) *J. Virol.* 61:3096. Another exemplary AAV vector is the Double-D ITR vector. Construction of the Double D ITR vector is disclosed in U.S. Pat. No. 5,478,745. Still other vectors are those disclosed in Carter, U.S. Pat. No. 4,797,368 and Muzyczka, U.S. Pat. No. 5,139,941, Chartejee, U.S. Pat. No. 5,474,935, and Kotin, PCT Patent Publication WO 94/288157. Yet a further example of an AAV vector employable in this invention is SSV9AFABTKneo, which contains the AFP enhancer and albumin promoter and directs expression predominantly in the liver. Its structure and construction are disclosed in SU, (1996) *Human Gene Therapy* 7:463–470. Additional AAV gene therapy vectors are described in U.S. Pat. No. 5,354,678, U.S. Pat. No. 5,173, 414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP 0176170 (Roizman). Additional exemplary herpes simplex virus vectors include HFEM/ ICP6-LacZ disclosed in WO 95/04139 (Wistar Institute), pHSVlac described in Geller et al. (1988) *Science* 241:1667–1669 and in WO 90/09441 and WO 92/07945, HSV Us3::pgC-lacZ described in Fink, (1992) *Human Gene Therapy* 3:11–19 and HSV 7134, 2 RH 105 and GAL4 described in EP 0453242 (Breakefield), and those deposited with the ATCC as accession numbers ATCC VR-977 and ATCC VR-260.

Also contemplated are alpha virus gene therapy vectors that can be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5,217,879, and WO 92/10578, WO 95/07994, U.S. Pat. No. 5,091,309 and U.S. Pat. No. 5,217,879 are employable. Such alpha viruses may be obtained from depositories or collections such as the ATCC in Rockville, Maryland or isolated from known sources using commonly available techniques. Preferably, alphavirus vectors with reduced cytotoxicity are used (see co-owned U.S. Ser. No. 08/679640).

DNA vector systems such as eukaryotic layered expression systems are also useful for expressing the nucleic acids of the invention. See WO 95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans et al. (1989) *Nature* 339:385 and Sabin et al. (1973) *J. Biol. Standardization* 1:115; rhinovirus, for example ATCC VR-1110 and those described in Arnold et al. (1990) *J. Cell Biochem* L40 1; pox viruses such as canary pox virus or vaccinia virus, for example ATCC VR-111 and ATCC VR-2010 and those described in Fisher-Hoch et al. (1989) *Proc. Natl. Acad. Sci.* 86:317; Flexner et al. (1989) *Ann. NY Acad. Sci.* 569:86; Flexner et al. (1990) *Vaccine* 8:17; in U.S. Pat. No. 4,603, 112 and U.S. Pat. No. 4,769,330 and in WO 89/01973; SV40 virus, for example ATCC VR-305 and those described in Mulligan et al. (1979) *Nature* 277:108 and Madzak et al. (1992) *J. Gen. Vir.* 73:1533; influenza virus, for example ATCC VR-797 and recombinant influenza viruses made employing reverse genetics techniques as described in U.S. Pat. No. 5,166,057 and in Enami et al. (1990) *Proc. Natl. Acad. Sci.* 87:3802–3805, Enami et al. (1991) *J. Virol.* 65:2711–2713; Luytjes et al. (1989) *Cell* 59:110 (see also McMicheal, (1983) NE *J. Med.* 309:13 and Yap et al. (1978) *Nature* 273:238 and Yap et al. (1979) *Nature* 277:108); human immunodeficiency virus as described in EP 0386882 and in Buchshacher et al. (1992) *J. Vir.* 66:2731; measles virus, for example ATCC VR-67 and VR-1247 and those described in EP 0440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR-66; Mucambo virus, for example ATCC VR-580 and ATCC VR-1244; Ndumu virus, for example ATCC VR-371; Pixuna virus, for example ATCC VR-372 and ATCC VR-1245; Tonate virus, for example ATCC VR-925; Triniti virus, for example ATCC VR-469; Una virus, for example ATCC VR-374; Whataroa virus, for example ATCC VR-926; Y-62–33 virus, for example ATCC VR-375; O'Nyong virus, Eastern encephalitis virus, for example ATCC VR-65f and ATCC VR-1242; Western encephalitis virus, for example ATCC VR-70, ATCC VR-1251, ATCC VR-622 and ATCC VR-1252; and coronavirus, for example ATCC VR-740 and those described in Hamre et al. (1966) *Proc. Soc. Exp. Biol. Med.* 121:190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel et al. (1989) *Hum. Gene Ther.* 3:147–154; ligand linked DNA, for example see Wu et al. (1989) *J. Biol. Chem.* 264:16985–16987, eucaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655; ionizing radiation as described in U.S. Pat. No. 5,206,152 and in WO 92/11033, nucleic charge neutralization or fusion with cell membranes. Additional approaches are described in Philip et al. (1994) *Mol. Cell Biol.* 14:2411–2418 and in Woffendin et al. (1994) *Proc. Natl. Acad. Sci.* 91:1581–1585.

Particle mediated gene transfer may be employed, for example see U.S. Ser. No. 60/023,867. Briefly, the sequence can be inserted into conventional vectors that contain conventional control sequences for high level expression, and then incubated with synthetic gene transfer molecules such as polymeric DNA-binding cations like polylysine, protamine, and albumin, linked to cell targeting ligands such as asialoorosomucoid, as described in Wu et al. (1987) *J. Biol. Chem.* 262:4429–4432, insulin as described in Hucked, (1990) *Biochem. Pharmacol.* 40:253–263, galactose as described in Plank et al. (1992) *Bioconjugate Chem.* 3:533–539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO 95/13796, WO 94/23697, WO 91/144445 and EP 524,968. As described in co-owned U.S. Ser. No. 60/023,867, on non-viral delivery, the nucleic acid sequences encoding a polypeptide can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al. (1994) *Proc. Natl. Acad. Sci. U.S.A.* 91 (24):11581–11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO 92/11033.

Exemplary liposome and polycationic gene delivery vehicles are those described in U.S. Pat. Nos. 5,422,120 and 4,762,915; in WO 95/13796; WO 94/23697; and WO 91/14445; in EP 0524968; and in Stryer et al. (1975) *Biochemistry*, pp. 236–240, W. H. Freeman, San Francisco; Szoka et al. (1980) *Biochim. Biophys. Acta.* 600:1; Bayer, (1979) *Biochim. Biophys. Acta.* 550:464; Rivnay et al. (1987) *Meth. Enzymol.* 149:119; Wang et al. (1987) *Proc. Natl. Acad. Sci.* 84:7851; Plant (1989) *Anal. Biochem.* 176:420.

Pharmaceutical Compositions

In addition to the pharmaceutically acceptable carriers and salts described above, the following additional agents can be used with polynucleotide compositions.

A. Polypeptides

One example is polypeptides which include, without limitation: asioloorosomucoid (ASOR); transferrin; asialoglycoproteins; antibodies; antibody fragments; ferritin; interleukins; interferons, granulocyte, macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of plasmodium falciparum known as RII.

B. Hormones, Vitamins, Etc.

Other groups that can be included are, for example: hormones, steroids, androgens, estrogens, thyroid hormone, or vitamins, folic acid.

C. Polyalkylenes, Polysaccharides, Etc.

Also, polyalkylene glycol can be included with the desired polynucleotides. In a preferred embodiment, the polyalkylene glycol is polyethylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug et al. (1991) *Biochim. Biophys. Acta.* 1097:1–17; Straubinger et al. (1983) *Methods of Enzymology* 101:512–527.

Liposomal preparations for use in the instant invention include cationic (positively charged), anionic (negatively charged) and neutral preparations.

Cationic liposomes have been shown to mediate intracellular delivery of plasmid DNA (Felgner et al. (1987) *Proc. Natl. Acad. Sci. U.S.A.* 84:7413–7416); mRNA (Malone et al. (1989) *Proc. Natl. Acad. Sci. U.S.A.* 86:6077–6081); and purified transcription factors (Debs et al. 1990) *J. Biol. Chem.* 265:10189–10192), in finctional form.

Cationic liposomes are readily available. For example, N[1–2,3-dioleyloxy)propyl]-N,N,N-triethylammonium (DOTMA) liposomes are available under the trademark Lipofectin, from GIBCO BRL, Grand Island, N.Y. (See, also, Felgner et al. (1987) *Proc. Natl. Acad. Sci. U.S.A.* 84:7413–7416). Other commercially available liposomes include transfectace (DDAB/DOPE) and DOTAP/DOPE (Boerhinger). Other cationic liposomes can be prepared from readily available materials using techniques well known in the art. See, e.g., Szoka et al. (1978) *Proc. Natl. Acad. Sci. U.S.A.* 75:4194–4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoyfphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al. (1983) *Methods of Immunology* 101:512–527; Szoka et al. (1978) *Proc. Natl. Acad. Sci. U.S.A.* 75:4194–4198; Papahadjopoulos et al. (1975) *Biochim. Biophys. Acta.* 394:483; Wilson et al. (1979) *Cell* 17:77; Deamer et al. (1976) *Biochim. Biophys. Acta.* 443:629; Ostro et al. (1977) *Biochem. Biophys. Res. Commun.* 76:836; Fraley et al. (1979) *Proc. Natl. Acad. Sci. U.S.A.* 76:3348; Enoch et al. (1979) *Proc. Natl. Acad. Sci. U.S.A.* 76:145; Fraley et al. (1980) *J. Biol. Chem.* 255:10431; Szoka et al. (1978) *Proc. Natl. Acad. Sci. U.S.A.* 75:145; and Schaefer-Ridder et al. (1982) *Science* 215:166.

E. Liproproteins

In addition, lipoproteins can be included with the polynucleotide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are included with the polynucleotide to be delivered, no other targeting ligand is included in the composition.

Naturally occurring lipoproteins comprises of a lipid and a protein portion. The protein portion is known as apoproteins. At the present, apoproteins A, B, C, D, and E have been isolated and identified. At least two of these contain several proteins, designated by Roman numerals, AI, AII, AIV, CI, CII, and CIII.

A lipoprotein can comprise more than one apoprotein. For example, naturally occurring chylomicrons comprises of A, B, C, and E; over time these lipoproteins lose A and acquire C and E apoproteins. VLDL comprises A, B, C, and E apoproteins; LDL comprises apoprotein B; and HDL comprises apoproteins A, C, and E.

The amino acids of these apoproteins are known and are described in, for example, Breslow (1985) *Annu. Rev. Biochem.* 54:699; Law et al. (1986) *Adv. Exp. Med. Biol.* 151:162; Chenetal. 1986) *J. Biol. Chem.* 261:12918;

Kane et al. (1980) *Proc. Natl. Acad. Sci. U.S.A.* 77:2465; and Utermann et al. (1984) *Hum. Genet.* 65:232.

Lipoproteins contain a variety of lipids including triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in *Meth. Enzym.* 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzy.*, Supra; Pitas et al. (1980) *J. Biochem.* 255:5454–5460; and Mahey et al. (1979) *J. Clin. Invest.* 64:743–750.

Lipoproteins can also be produced by in vitro or recombinant methods by expression of the apoprotein genes in a desired host cell. See, for example, Atkinson et al. (1986) *Annu. Rev. Biophys. Chem.* 15:403 and Radding et al. (1958) *Biochim. Biophys. Acta.* 30:443.

Lipoproteins can also be purchased from commercial suppliers, such as Biomedical Technologies, Inc., Stoughton, Mass., U.S.A.

Further description of lipoproteins can be found in Zuckermann et al., PCT. application No. U.S. Pat. No. 97/14465.

F. Polycationic Agents

Polycationic agents can be included, with or without lipoprotein, in a composition with the desired polynucleotide to be delivered.

Polycationic agents, typically exhibit a net positive charge at physiological relevant pH and are capable of neutralizing the electrical charge of nucleic acids to facilitate delivery to a desired location. These agents have in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyomithine, and protamine. Other examples include histones, protamines, human serum albumin, DNA binding proteins, non-histone chromosomal proteins, coat proteins from DNA viruses, such as φX174, transcriptional factors also contain domains that bind DNA and therefore may be useful as nucleic acid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and putrescine.

The dimensions and the physical properties of a polycationic agent can be extrapolated from the list above to construct other polypeptide polycationic agents or to produce synthetic polycationic agents.

Synthetic Polycationic Agents

Synthetic polycationic agents which are useful include, for example, DEAE-dextran, polybrene. Lipofectin, and lipofectAMINE are monomers that form polycationic complexes when combined with polynucleotides. See for example, Zuckermann et al., PCT application U.S. Pat. No. 97/14465.

A polynucleotide composition can comprises therapeutically effective amount of a gene therapy vehicle, as the term is defined above. For purposes of the present invention, an effective dose will be from about 0.01 mg/kg to 50 mg/kg or 0.05 mg/kg to about 10 mg/kg of the DNA constructs in the individual to which it is administered.

Delivery Methods

Once formulated, the polynucleotide compositions of the invention can be administered (1) directly to the subject; (2) delivered ex vivo, to cells derived from the subject; or (3) in vitro for expression of recombinant proteins. The subjects to be treated can be mammals or birds. Also, human subjects can be treated.

Direct delivery of the compositions will generally be accomplished by injection, either subcutaneously, intraperitoneally, intravenously or intramuscularly or delivered to the interstitial space of a tissue. The compositions can also be administered into a tumor or lesion. Other modes of administration include oral and pulmonary administration, suppositories, and transdermal applications, needles, and gene guns or hyposprays. Dosage treatment may be a single dose schedule or a multiple dose schedule.

Methods for the ex vivo delivery and reimplantation of transformed cells into a subject are known in the art and described in e.g., International Publication No. WO 93/14778. Examples of cells useful in ex vivo applications include, for example, stem cells, particularly hematopoietic, lymph cells, macrophages, dendritic cells, or tumor cells.

Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

EXAMPLES

The examples presented below are provided as a further guide to the practitioner of ordinary skill in the art, and are not to be construed as limiting the invention in any way.

Example 1

Cloning and Sequence Analysis of Myosin IXa

In order to identify novel transcripts in the human chromosomal region 15p22-23 which could be candidates for the Bardet-Biedl Sydrome gene that maps to this locus (BBS4; Bruford et al. (1997) *Genomics* 41:83–99) a BAC contig spanning this locus was constructed. A random clone sublibrary was generated for each BAC. BAC clones forming a contig across the chromosome 15q22-23 region were cleaved with CviJI under conditions that produced partial restriction fragments ranging in size from ~500 bp to ~4 kb. Fragments in the 1–2 kb range were isolated and cloned into the vector Perfectly Blunt™ (Novagen). For each BAC, 192 clones were randomly selected and sequenced using the ABI TAQ dye chemistry/system.

Comparison of these high throughput sample sequences originating from human chromosome 15 showed homology with 5 human EST clones (accession numbers AA287851, AA79085, AA235795, AA368273, HUMM9AA) and with myosin IXa (accession number L29148). Several clones were identified that showed significant homology to myr5 and human myosin IXb, and 100% identity to the entire 250 bp sequence known for human myosin IXa. Myosin IXa had previously been mapped to human chromosome 15q21-q25. Based on the information obtained from the comparisons of the myosin IXb sequence to the sequences of the inserts in these BAC sub-libraries, PCR primers were designed for Marathon™ 5' and 3' RACE™ reactions using Marathon™ prepared leukocyte, retina and testis cDNA (Clontech) as templates. Resulting fragments were cloned into pCRII (Invitrogen), sequenced and used for primer design for subsequent Marathon™ reactions. Nucleotide sequence for both strands of the partial cDNAs was obtained using the ABI TAQ dye terminator chemistry/system. Sequence comparison analysis was done using MASPAR and GeneWorks™ (Intelligenetics).

A sequence representing a transcript of 8473 bp was obtained. Human myosin IXa was mapped on the Stanford G3 radiation hybrid panel using oligos having homology to myosin IXa cDNA. Duplicate reactions consistently linked this region of myosin IXa to marker SHGC-31014 located on chromosome 15 in bin #50 confirming that the myosin IXa gene is located on human chromosome 15q21.

An ATG is present at base 243 and is in good context having an A at the -3 position and a G at +4 (Kozak et al. (1995)). This ATG initiates a single ORF that continues for 7643 bases to a stop signal (UGA) present at base 7886. Sequence analysis and exon mapping of the myo IXa transcript indicated that myosin IXa contains 42 exons and predicts a protein of 2548 amino acids with an estimated molecular mass of 283 kDa (FIG. 1), a size similar to the myosin lXb gene product (Wirth et al. (1996)).

The myosin IXa gene spans over 185 kb in the human genome (data not shown) and produces a transcript whose predicted protein contains the domains described for class IX unconventional myosins. To determine the similarity between family members, the predicted amino acid sequence of human myosin IXa, myosin IXb, and rat myr5 were compared. The N-terminal extension of myosin IXa shares 40% identity with the other class IX myosins. Myosin IXa had 82% identity with myosin IXb and myr5 within the head domain that is conserved among known myosin classes, although myosin IXa also contained an 18 residue insertion absent in the other class IX family members. The position designated as the second flexible loop (20/50 kDa junction; which is proposed to contact actin (Rayment et al. (1993); Schroder et al. (1993)) and is the site of the second insertion in the head region of the class IX myosins, contained an additional 32 residues in myosin IXa in addition to having only 31% homology within the 120 residues shared with myosin IXb and myr5.

Within the neck region, myosin IXa contained two separate insertions of 33 and 18 residues compared to the other class IX family members. These insertions conform to the "IQ motif" and suggest that myosin IXa may bind 6 light chains of the clamodulin/EF hand superfamily (Mercer et al. 1991) instead of the 4 predicted to bind to myosin IXb and myr5.

The tail region of myosin IXa has 58% identity with the GAP domain found in myr5 and myosin IXb. However, the tail region located between the neck region and the GAP domain has numerous insertions not found in the other class IX family members that add an additional 327 residues compared to myr5 or 286 residues compared to myosin IXb.

Example 2

Expression of Myo IXa

To determine the expression profile of myosin IXa, human tissue Northern blots were hybridized with three different probes that represented the myosin IXa N-terminal extension plus a small portion of the conserved head domain, the GAP domain and the 3' untranslated region. Briefly, human northern analysis was conducted on MTN Human, Human II and Human Brain II blots (Clontech). Probes corresponding to bases 9–1081, 6141–6831, and 7854–8304 were prepared using Amersham's Rediprime™ kit with $^{32}P\alpha dCTP$, hybridized in Express Hybridization solution (Clontech) as described by the manufacturer and exposed to BioMax™ film (Amersham).

A transcript of ~12.5 kb was visible in all tissues tested except liver. In addition, a transcript of ~8.5 kb was present in testis and placenta. To ascertain whether the 4 kb difference between the two testis messages involved alternative splicing and/or polyadenylation at the 3' region of the message, Marathon™ cDNA (Clontech) from testis, whole brain and cerebellum was amplified using a primer specific to the last exon (to bases 7704–7727) and the MarathonTm adaptor primer AP1. This PCR reaction produced a single band in all cases which corresponded to the product predicted from the cloned sequence. In addition, two brain cDNA libraries (frontal cortex and cerebellum (Stratagene)) were screened using the GAP domain probe. No evidence was found for either alternative splicing or polyadenylation at the 3' end of the myosin IXa transcript. Alternative splicing within and/or between the remaining identified exons was ruled out by conducting PCR amplification of whole brain, cerebellum, retina and testis cDNA with primers that spanned intron/exon junctions. No differences in product sizes were seen between those tissues expressing only the 12.5 kb transcript and testis. This result was confirmed by conducting multiple hybridizations to a frontal cortex cDNA library using probes representing each portion of the myosin IXA transcript. Thus, the 4 kb difference between the two transcript sizes present in testis was not due to alternative splicing between the identified exons nor due to alternative polyadenylation and most likely resides in the 5' untranslated region of the myosin IXa transcript. Therefore, the additional 4 kb present in the larger transcript is likely located in the 5' UTR.

However, at least one alternative splicing event does occur within the myosin IXa coding region. During the cloning, two distinct bands were generated from PCR reactions conducted on leukocyte cDNA with primers specific to the head region. Sequence analysis of these bands indicated that a cryptic splice site exists at bases 375–380 and acts as a splice donor site, creating a truncated exon #2. Identical PCR reactions conducted on cDNA from testis and retina produced only the larger product. This data suggests that a second protein may be present in leukocytes, arising from an alternative splice within the second exon, which truncates the N-terminal extension and eliminates the ATTP binding domain of the myosin head region. No unique transcript for the predicted truncated protein was visible on Northern blots, presumably due to the decreased separation of molecules in the 12.0–12.5 kb size range.

Example 3

Developmental Expression of Myo IXa in a Mouse Model

A fragment specific to the mouse N-terminal extension of myosin Ixa was obtained by conducting a PCR reaction on mouse genomic DNA using primers corresponding to bases 252.271 and bases 608–590 of the human myosin IXa sequence. This probe was prepared as described above and hybridized to mouse poly A+ Northern blots prepared using standard methods from freshly dissected tissues. A single transcript of ~9 kb was detected. Myosin IXa was first visible in RNA from 11.5 d embryos, absent from 13.5 d embryos and reappeared in 15.5 d embryos. Myosin IXa was also present in RNA obtained from 13.5 d old limb buds and brain. Adult tissues also showed a myo IXa transcript of ~9 kb expressed in brain, heart, skeletal muscle, retina, leukocytes, lung, kidney, thymus and testis. No message was present in liver, a pattern identical with that seen in adult human tissues.

Example 4

Myo IXa Functions as a GTPase Activating Protein

Myr5 acts as a GTP activating protein on members of the rho subfamily of GTP binding proteins (Reinhard et al. (1995) *EMBO J*. 14:697–704). We determined that myosin IXa is also a functional GAP by making an expression construct that contained the predicted GAP domain (bases 6141 to 8035 of SEQ ID NO: 2) and conducting GAP assays with the small GTP binding proteins rhoA, ras, rac and Cdc42.

Example 5

Cloning and Sequence Analysis of CNGC-15 cDNA

A partial CNGC-15 cDNA, 1281 nucleotides in length was isolated from a human BAC contigs as described in Example 1. The cDNA sequence is shown in FIG. 3. The ATG codon at nucleotide 36 g initiates an open reading frame that contiues through the rest of the cDNA. Comparison of the nucleotide to Genbank, EST and patent databases showed that this partial cDNA has 76.2% homology to a mouse ion channel BCGN-3 mRNA (Genbank accession number AF064874) and lesser homology to mouse and human ion channels. The longest stretch of 100% homology with sequences in the databases was 44 nucleotides.

What is claimed is:

1. An isolated nucleic acid molecule comprising a polynucleotide selected from the group consisting of:
   a) a polynucleotide encoding the amino acid sequence of SEQ ID NO:1;
   b) a polynucleotide comprising SEQ ID NO:2;
   c) a polynucleotide comprising at least about 390 contiguous bases from the coding region of SEQ ID NO:2;
   d) a polynucleotide consisting of nucleotides 243–7085 of SEQ ID NO:2;
   e) a polynucleotide consisting of nucleotides 243–680 of SEQ ID NO:2;
   f) a polynucleotide consisting of nucleotides 683–2399 of SEQ ID NO:2;
   g) a polynucleotide consisting of nucleotides 2402–2747 of SEQ ID NO:2;
   h) a polynucleotide consisting of nucleotides 3158–3740 of SEQ ID NO:2; and
   i) a polynucleotide consisting of nucleotides 6473–6899 of SEQ ID NO:2.

2. An expression vector comprising the isolated nucleic acid molecule of claim 1 wherein said isolated nucleic acid molecule is operably linked to a promoter.

3. A transformed cell having stably incorporated into its genome the expression vector of claim 2.

4. A method for producing a Myosin IXa polypeptide or a derivative thereof, comprising:
   a) providing a host cell stably transformed with an expression vector comprising a promoter operably linked to an isolated nucleic acid molecule encoding said Myosin IXa polypeptide or derivative thereof; and
   b) culturing the host cell under conditions which allow expression of said polypeptide.

5. An isolated nucleic acid molecule comprising a polynucleotide selected from the group consisting of:
   (a) a polynucleotide encoding SEQ ID NO:1;
   (b) a polynucleotide encoding amino acids from 1 to 146 of SEQ ID NO:1;
   (c) a polynucleotide encoding amino acids from about 147 to about 719 of SEQ ID NO:1;
   (d) a polynucleotide encoding amino acids from about 720 to about 835 of SEQ ID NO:1;
   (e) a polynucleotide encoding amino acids from about 972 to about 1166 of SEQ ID NO:1; and
   (f) a polynucleotide encoding amino acids from about 2074 to about 2219 of SEQ ID NO:1.

6. An isolated nucleic acid molecule encoding a fusion protein, wherein the nucleic acid molecule according to (a), (b), (c), (d), (e) or (f) of claim 5 encoding a polypeptide fragment is in-frame with a polynucleotide encoding a polypeptide of interest.

7. An expression vector comprising the isolated nucleic acid molecule of claim 6 wherein said isolated nucleic acid molecule is operably linked to a promoter.

8. A transformed cell having stably incorporated into its genome the expression vector of claim 7.

9. An isolated nucleic acid molecule comprising a polynucleotide encoding a polypeptide wherein, except for at least one conservative amino acid substitution, said polypeptide has an amino acid sequence selected from the group consisting of:

a) amino acids of SEQ ID NO:1;

b) amino acids from 1 to [about] 146 of SEQ ID NO:1;

c) amino acids from about 147 to about 719 of SEQ ID NO:1;

d) amino acids from about 720 to about 835 of SEQ ID NO:1;

e) amino acids from about 972 to about 1166 of SEQ ID NO:1; and f) amino acids from about 2074 to about 2219 of SEQ ID NO:1 wherein said polypeptide retains at least 40% of at least one of the activities of Myosin IXa selected from the group consisting of ATP binding, ATPase activity zinc binding, calmodulin/EF binding, GTPase activity, membrane binding, phorbol ester binding, and synthesis of phosphatidylinositol-4,5-bis-phosphate.

* * * * *

SEQUENCE LISTING

<160> NUMBER OF SEQ ID NOS: 3

<210> SEQ ID NO 1
<211> LENGTH: 2548
<212> TYPE: PRT
<213> ORGANISM: Homo sapien

<400> SEQUENCE: 1

```
Met Asn Ile Asn Asp Gly Gly Arg Arg Phe Glu Asp Asn Glu His
 1               5                  10                  15

Thr Leu Arg Ile Tyr Pro Gly Ala Ile Ser Glu Gly Thr Ile Tyr Cys
                20                  25                  30

Pro Ile Pro Ala Arg Lys Asn Ser Thr Ala Ala Glu Val Ile Glu Ser
                35                  40                  45

Leu Ile Asn Lys Leu His Leu Asp Lys Thr Lys Cys Tyr Val Leu Ala
 50                  55                  60

Glu Val Lys Glu Phe Gly Gly Glu Glu Trp Ile Leu Asn Pro Thr Asp
 65                  70                  75                  80

Cys Pro Val Gln Gln Met Met Leu Trp Pro Arg Met Ala Leu Glu Asn
                85                  90                  95

Arg Leu Ser Gly Glu Asp Tyr Arg Phe Leu Leu Arg Glu Lys Asn Leu
                100                 105                 110

Asp Gly Ser Ile His Tyr Gly Ser Leu Gln Ser Trp Leu Arg Val Thr
                115                 120                 125

Glu Glu Arg Arg Arg Met Met Glu Arg Gly Phe Leu Pro Gln Pro Gln
                130                 135                 140

Gln Lys Asp Phe Asp Asp Leu Cys Ser Leu Pro Asp Leu Asn Glu Lys
145                 150                 155                 160

Thr Leu Leu Glu Asn Leu Arg Asp Arg Phe Lys His Glu Lys Ile Tyr
                165                 170                 175

Thr Tyr Val Gly Ser Ile Leu Ile Val Ile Asn Pro Phe Lys Phe Leu
                180                 185                 190

Pro Ile Tyr Asn Pro Lys Tyr Val Lys Met Tyr Asp Asn His Gln Leu
                195                 200                 205

Gly Lys Pro Glu Pro His Ile Tyr Ala Val Ala Asp Val Ala Tyr His
                210                 215                 220

Ala Met Leu Gln Arg Lys Lys Asn Gln Cys Ile Val Ile Ser Gly Glu
225                 230                 235                 240

Ser Gly Ser Gly Lys Thr Gln Ser Thr Asn Phe Leu Ile His Leu
                245                 250                 255

Thr Ala Leu Ser Gln Lys Gly Phe Ala Ser Gly Val Glu Gln Ile Ile
                260                 265                 270

Leu Gly Ala Gly Pro Val Leu Glu Ala Phe Gly Asn Ala Lys Thr Ala
                275                 280                 285

His Asn Asn Asn Ser Ser Arg Phe Gly Lys Phe Ile Gln Val Asn Tyr
                290                 295                 300

Gln Glu Thr Gly Thr Val Leu Gly Ala Tyr Val Glu Lys Tyr Leu Leu
305                 310                 315                 320

Glu Lys Ser Arg Leu Val Tyr Gln Glu His Asn Glu Arg Asn Tyr His
                325                 330                 335

Val Phe Tyr Tyr Leu Leu Ala Gly Ala Ser Glu Asp Glu Arg Ser Ala
                340                 345                 350

Phe His Leu Lys Gln Pro Glu Glu Tyr His Tyr Leu Asn Gln Ile Thr
```

-continued

```
            355                 360                 365
Lys Lys Pro Leu Arg Gln Ser Trp Asp Asp Tyr Cys Tyr Asp Ser Glu
            370                 375                 380
Pro Asp Cys Phe Thr Val Glu Gly Glu Asp Leu Arg His Asp Phe Glu
385                 390                 395                 400
Arg Leu Gln Leu Ala Met Glu Met Val Gly Phe Leu Pro Lys Thr Arg
                    405                 410                 415
Arg Gln Ile Phe Ser Leu Leu Ser Ala Ile Leu His Leu Gly Asn Ile
                420                 425                 430
Cys Tyr Lys Lys Lys Thr Tyr Arg Asp Asp Ser Ile Asp Ile Cys Asn
            435                 440                 445
Pro Glu Val Leu Pro Ile Val Ser Glu Leu Leu Glu Val Lys Glu Glu
450                 455                 460
Met Leu Phe Glu Ala Leu Val Thr Arg Lys Thr Val Thr Val Gly Glu
465                 470                 475                 480
Lys Leu Ile Leu Pro Tyr Lys Leu Ala Glu Ala Val Thr Val Arg Asn
                485                 490                 495
Ser Met Ala Lys Ser Leu Tyr Ser Ala Leu Phe Asp Trp Ile Val Phe
            500                 505                 510
Arg Ile Asn His Ala Leu Leu Asn Ser Lys Asp Leu Glu His Asn Thr
            515                 520                 525
Lys Thr Leu Ser Ile Gly Val Leu Asp Ile Phe Gly Phe Glu Asp Tyr
            530                 535                 540
Glu Asn Asn Ser Phe Glu Gln Phe Cys Ile Asn Phe Ala Asn Glu Arg
545                 550                 555                 560
Leu Gln His Tyr Phe Asn Gln His Ile Phe Lys Leu Glu Gln Glu Glu
                565                 570                 575
Tyr Arg Thr Glu Gly Ile Ser Trp His Asn Ile Asp Tyr Ile Asp Asn
            580                 585                 590
Thr Cys Cys Ile Asn Leu Ile Ser Lys Lys Pro Thr Gly Leu Leu His
            595                 600                 605
Leu Leu Asp Glu Glu Ser Asn Phe Pro Gln Ala Thr Asn Gln Thr Leu
            610                 615                 620
Leu Asp Lys Phe Lys His Gln His Glu Asp Asn Ser Tyr Ile Glu Phe
625                 630                 635                 640
Pro Ala Val Met Glu Pro Ala Phe Ile Ile Lys His Tyr Ala Gly Lys
                645                 650                 655
Val Lys Tyr Gly Val Lys Asp Phe Arg Glu Lys Asn Thr Asp His Met
                660                 665                 670
Arg Pro Asp Ile Val Ala Leu Leu Arg Ser Ser Lys Asn Ala Phe Ile
            675                 680                 685
Ser Gly Met Ile Gly Ile Asp Pro Val Ala Val Phe Arg Trp Ala Ile
            690                 695                 700
Leu Arg Ala Phe Phe Arg Ala Met Val Ala Phe Arg Glu Ala Gly Lys
705                 710                 715                 720
Arg Asn Ile His Arg Lys Thr Gly His Asp Asp Thr Ala Pro Cys Ala
                    725                 730                 735
Ile Leu Lys Ser Met Asp Ser Phe Ser Phe Leu Gln His Pro Val His
                740                 745                 750
Gln Arg Ser Leu Glu Ile Leu Gln Arg Cys Lys Glu Glu Lys Tyr Ser
            755                 760                 765
Ile Thr Arg Lys Asn Pro Arg Thr Pro Leu Ser Asp Leu Gln Gly Met
            770                 775                 780
```

-continued

Asn Ala Leu Asn Glu Lys Asn Gln His Asp Thr Phe Asp Ile Ala Trp
785                 790                 795                 800

Asn Gly Arg Thr Gly Ile Arg Gln Ser Arg Leu Ser Ser Gly Thr Ser
            805                 810                 815

Leu Leu Asp Lys Asp Gly Ile Phe Ala Asn Ser Thr Ser Ser Lys Leu
            820                 825                 830

Leu Glu Arg Ala His Gly Ile Leu Thr Arg Asn Lys Asn Phe Lys Ser
            835                 840                 845

Lys Pro Ala Leu Pro Lys His Leu Leu Glu Val Asn Ser Leu Lys His
    850                 855                 860

Leu Thr Arg Leu Thr Leu Gln Asp Arg Ile Thr Lys Ser Leu Leu His
865                 870                 875                 880

Leu His Lys Lys Lys Pro Pro Ser Ile Ser Ala Gln Phe Gln Ala
                885                 890                 895

Ser Leu Ser Lys Leu Met Glu Thr Leu Gly Gln Ala Glu Pro Tyr Phe
            900                 905                 910

Val Lys Cys Ile Arg Ser Asn Ala Glu Lys Leu Pro Leu Arg Phe Ser
            915                 920                 925

Asp Val Leu Val Leu Arg Gln Leu Arg Tyr Thr Gly Met Leu Glu Thr
930                 935                 940

Val Gln Ile Arg Gln Ser Gly Tyr Ser Ser Lys Tyr Ser Phe Gln Asp
945                 950                 955                 960

Phe Val Ser His Phe His Val Leu Leu Pro Arg Asn Ile Ile Pro Ser
            965                 970                 975

Lys Phe Asn Ile Gln Asp Phe Phe Arg Lys Ile Asn Leu Asn Pro Asp
            980                 985                 990

Asn Tyr Gln Val Gly Lys Thr Met Val Phe Leu Lys Glu Gln Glu Arg
            995                 1000                1005

Gln His Leu Gln Asp Leu Leu His Gln Glu Val Leu Arg Arg Ile Ile
    1010                1015                1020

Leu Leu Gln Arg Trp Phe Arg Val Leu Leu Cys Arg Gln His Phe Leu
1025                1030                1035                1040

His Leu Arg Gln Ala Ser Val Ile Ile Gln Arg Phe Trp Arg Asn Tyr
            1045                1050                1055

Leu Asn Gln Lys Gln Val Arg Asp Ala Ala Val Gln Lys Asp Ala Phe
            1060                1065                1070

Val Met Ala Ser Ala Ala Ala Leu Leu Gln Ala Ser Trp Arg Ala His
            1075                1080                1085

Leu Glu Arg Gln Arg Tyr Leu Glu Leu Arg Ala Ala Ala Ile Val Ile
    1090                1095                1100

Gln Gln Lys Trp Arg Asp Tyr Tyr Arg Arg Arg His Met Ala Ala Ile
1105                1110                1115                1120

Cys Ile Gln Ala Arg Trp Lys Ala Tyr Arg Glu Ser Lys Arg Tyr Gln
            1125                1130                1135

Glu Gln Arg Lys Lys Ile Ile Leu Leu Gln Ser Thr Cys Arg Gly Phe
            1140                1145                1150

Arg Ala Arg Gln Arg Phe Lys Ala Leu Lys Glu Gln Arg Leu Arg Glu
            1155                1160                1165

Thr Lys Pro Glu Val Gly Leu Val Asn Ile Lys Gly Tyr Gly Ser Leu
    1170                1175                1180

Glu Ile Gln Gly Ser Asp Pro Ser Glu Trp Glu Asp Cys Ser Phe Asp
1185                1190                1195                1200

-continued

```
Asn Arg Ile Lys Ala Ile Glu Glu Cys Lys Ser Val Ile Glu Ser Asn
            1205                1210                1215
Arg Ile Ser Arg Glu Ser Ser Val Asp Cys Leu Lys Glu Ser Pro Asn
            1220                1225                1230
Lys Gln Gln Glu Arg Ala Gln Ser Gln Ser Gly Val Asp Leu Gln Glu
            1235                1240                1245
Asp Val Leu Val Arg Glu Arg Pro Arg Ser Leu Glu Asp Leu His Gln
            1250                1255                1260
Lys Lys Val Gly Arg Ala Lys Arg Glu Ser Arg Arg Met Arg Glu Leu
1265                1270                1275                1280
Glu Gln Ala Ile Phe Ser Leu Glu Leu Leu Lys Val Arg Ser Leu Gly
            1285                1290                1295
Gly Ile Ser Pro Ser Glu Asp Arg Arg Trp Ser Thr Glu Leu Val Pro
            1300                1305                1310
Glu Gly Leu Gln Ser Pro Arg Gly Thr Pro Asp Ser Glu Ser Ser Gln
            1315                1320                1325
Gly Ser Leu Glu Leu Leu Ser Tyr Glu Glu Ser Gln Lys Ser Lys Leu
            1330                1335                1340
Glu Ser Val Ile Ser Asp Glu Gly Asp Leu Gln Phe Pro Ser Pro Lys
1345                1350                1355                1360
Ile Ser Ser Ser Pro Lys Phe Asp Ser Arg Asp Asn Ala Leu Ser Ala
            1365                1370                1375
Ser Asn Glu Thr Ser Ser Ala Glu His Leu Lys Asp Gly Thr Met Lys
            1380                1385                1390
Glu Met Val Val Cys Ser Ser Glu Ser Ile Thr Cys Lys Pro Gln Leu
            1395                1400                1405
Lys Asp Ser Phe Ile Ser Asn Ser Leu Pro Thr Phe Phe Tyr Ile Pro
            1410                1415                1420
Gln Gln Asp Pro Leu Lys Thr Asn Ser Gln Leu Asp Thr Ser Ile Gln
1425                1430                1435                1440
Arg Asn Lys Leu Leu Glu Asn Glu Asp Thr Ala Gly Glu Ala Leu Thr
            1445                1450                1455
Leu Asp Ile Asn Arg Glu Thr Arg Arg Tyr His Cys Ser Gly Lys Asp
            1460                1465                1470
Gln Ile Val Pro Ser Leu Asn Thr Glu Ser Ser Asn Pro Val Leu Lys
            1475                1480                1485
Lys Leu Glu Lys Leu Asn Thr Glu Lys Glu Glu Arg Gln Lys Gln Leu
            1490                1495                1500
Gln Gln Gln Asn Glu Lys Glu Met Met Glu Gln Ile Arg Gln Gln Thr
1505                1510                1515                1520
Asp Ile Leu Glu Lys Glu Arg Lys Ala Phe Lys Thr Ile Glu Lys Pro
            1525                1530                1535
Arg Ile Gly Glu Cys Leu Val Ala Pro Ser Ser Tyr Gln Ser Lys Gln
            1540                1545                1550
Arg Val Glu Arg Pro Ser Ser Leu Leu Ser Leu Asn Thr Ser Asn Lys
            1555                1560                1565
Gly Glu Leu Asn Val Leu Gly Ser Leu Ser Leu Lys Asp Ala Ala Leu
            1570                1575                1580
Ala Gln Lys Asp Ser Ser Ser Ala His Leu Pro Pro Lys Asp Arg Pro
1585                1590                1595                1600
Val Thr Val Phe Phe Glu Arg Lys Gly Ser Pro Cys Gln Ser Ser Thr
            1605                1610                1615
Val Lys Glu Leu Ser Lys Thr Asp Arg Met Gly Thr Gln Leu Asn Val
```

-continued

```
                1620                1625                1630
Ala Cys Lys Leu Ser Asn Asn Arg Ile Ser Lys Arg Glu His Phe Arg
            1635                1640                1645
Pro Thr Gln Ser Tyr Ser His Asn Ser Asp Asp Leu Ser Arg Glu Gly
    1650                1655                1660
Asn Ala Arg Pro Ile Phe Phe Thr Pro Lys Asp Asn Met Ser Ile Pro
1665                1670                1675                1680
Leu Val Ser Lys Glu Ala Leu Asn Ser Lys Asn Pro Gln Leu His Lys
            1685                1690                1695
Glu Asp Glu Pro Ala Trp Lys Pro Val Lys Leu Ala Gly Pro Gly Gln
    1700                1705                1710
Arg Glu Thr Ser Gln Arg Phe Ser Ser Val Asp Glu Gln Ala Lys Leu
    1715                1720                1725
His Lys Thr Met Ser Gln Gly Glu Ile Thr Lys Leu Ala Val Arg Gln
    1730                1735                1740
Lys Ala Ser Asp Ser Asp Ile Arg Pro Gln Arg Ala Lys Met Arg Phe
1745                1750                1755                1760
Trp Ala Lys Gly Lys Gln Gly Glu Lys Lys Thr Thr Arg Val Lys Pro
            1765                1770                1775
Thr Thr Gln Ser Glu Val Ser Pro Leu Phe Ala Gly Thr Asp Val Ile
            1780                1785                1790
Pro Ala His Gln Phe Pro Asp Glu Leu Ala Ala Tyr His Pro Thr Pro
            1795                1800                1805
Pro Leu Ser Pro Glu Leu Pro Gly Ser Cys Arg Lys Glu Phe Lys Glu
    1810                1815                1820
Asn Lys Glu Pro Ser Pro Lys Ala Lys Arg Lys Arg Ser Val Lys Ile
1825                1830                1835                1840
Ser Asn Val Ala Leu Asp Ser Met His Trp Gln Asn Asp Ser Val Gln
            1845                1850                1855
Ile Ile Ala Ser Val Ser Asp Leu Lys Ser Met Asp Glu Phe Leu Leu
            1860                1865                1870
Lys Lys Val Asn Asp Leu Asp Asn Glu Asp Ser Lys Lys Asp Thr Leu
            1875                1880                1885
Val Asp Val Val Phe Lys Lys Ala Leu Lys Glu Phe Arg Gln Asn Ile
    1890                1895                1900
Phe Ser Phe Tyr Ser Ser Ala Leu Ala Met Asp Asp Gly Lys Ser Ile
1905                1910                1915                1920
Arg Tyr Lys Asp Leu Tyr Ala Leu Phe Glu Gln Ile Leu Glu Lys Thr
            1925                1930                1935
Met Arg Leu Glu Gln Arg Asp Ser Leu Gly Glu Ser Pro Val Arg Val
            1940                1945                1950
Trp Val Asn Thr Phe Lys Val Phe Leu Asp Glu Tyr Met Asn Glu Phe
            1955                1960                1965
Lys Thr Ser Asp Cys Thr Ala Thr Lys Val Pro Lys Thr Glu Arg Lys
    1970                1975                1980
Lys Arg Arg Lys Lys Glu Thr Asp Leu Val Glu His Asn Gly His
1985                1990                1995                2000
Ile Phe Lys Ala Thr Gln Tyr Ser Ile Pro Thr Tyr Cys Glu Tyr Cys
            2005                2010                2015
Ser Ser Leu Ile Trp Ile Met Asp Arg Ala Ser Val Cys Lys Leu Cys
            2020                2025                2030
Lys Tyr Ala Cys His Lys Lys Cys Cys Leu Lys Thr Thr Ala Lys Cys
            2035                2040                2045
```

```
Ser Lys Lys Tyr Asp Pro Glu Leu Ser Ser Arg Gln Phe Gly Val Glu
    2050                2055                2060

Leu Ser Arg Leu Thr Ser Glu Asp Arg Thr Val Pro Leu Val Val Glu
2065                2070                2075                2080

Lys Leu Ile Asn Tyr Ile Glu Met His Gly Leu Tyr Thr Glu Gly Ile
                2085                2090                2095

Tyr Arg Lys Ser Gly Ser Thr Asn Lys Ile Lys Glu Leu Arg Gln Gly
                2100                2105                2110

Leu Asp Thr Asp Ala Glu Ser Val Asn Leu Asp Asp Tyr Asn Ile His
            2115                2120                2125

Val Ile Ala Ser Val Phe Lys Gln Trp Leu Arg Asp Leu Pro Asn Pro
            2130                2135                2140

Leu Met Thr Phe Glu Leu Tyr Glu Glu Phe Leu Arg Ala Met Gly Leu
2145                2150                2155                2160

Gln Glu Arg Lys Glu Thr Ile Arg Gly Val Tyr Ser Val Ile Asp Gln
                2165                2170                2175

Leu Ser Arg Thr His Leu Asn Thr Leu Glu Arg Leu Ile Phe His Leu
                2180                2185                2190

Val Arg Ile Ala Leu Gln Glu Asp Thr Asn Arg Met Ser Ala Asn Ala
            2195                2200                2205

Leu Ala Ile Val Phe Ala Pro Cys Ile Leu Arg Cys Pro Asp Thr Thr
            2210                2215                2220

Asp Pro Leu Gln Ser Val Gln Asp Ile Ser Lys Thr Thr Thr Cys Val
2225                2230                2235                2240

Glu Leu Ile Val Val Glu Gln Met Asn Lys Tyr Lys Ala Arg Leu Lys
                2245                2250                2255

Asp Ile Ser Ser Leu Glu Phe Ala Glu Asn Lys Ala Lys Thr Arg Leu
                2260                2265                2270

Ser Leu Ile Arg Arg Ser Met Gly Lys Gly Arg Ile Arg Arg Gly Asn
            2275                2280                2285

Tyr Pro Gly Pro Ser Ser Pro Val Val Arg Leu Pro Ser Val Ser
            2290                2295                2300

Asp Val Ser Glu Glu Thr Leu Thr Ser Glu Ala Ala Met Glu Thr Asp
2305                2310                2315                2320

Ile Thr Glu Gln Gln Gln Ala Ala Met Gln Gln Glu Arg Val Leu
                2325                2330                2335

Thr Glu Gln Ile Glu Asn Leu Gln Lys Glu Lys Glu Glu Leu Thr Phe
                2340                2345                2350

Glu Met Leu Val Leu Glu Pro Arg Ala Ser Asp Asp Glu Thr Leu Glu
            2355                2360                2365

Ser Glu Ala Ser Ile Gly Thr Ala Asp Ser Ser Glu Asn Leu Asn Met
    2370                2375                2380

Glu Ser Glu Tyr Ala Ile Ser Glu Lys Ser Glu Arg Ser Leu Ala Leu
2385                2390                2395                2400

Ser Ser Leu Lys Thr Ala Gly Lys Ser Glu Pro Ser Ser Lys Leu Arg
                2405                2410                2415

Lys Gln Leu Lys Lys Gln Gln Asp Ser Leu Asp Val Val Asp Ser Ser
                2420                2425                2430

Val Ser Ser Leu Cys Leu Ser Asn Thr Ala Ser Ser His Gly Thr Arg
            2435                2440                2445

Lys Leu Phe Gln Ile Tyr Ser Lys Ser Pro Phe Tyr Arg Ala Ala Ser
    2450                2455                2460
```

| | | | | | | | | | | |
|---|---|---|---|---|---|---|---|---|---|---|
|Gly|Asn|Glu|Ala|Leu|Gly|Met|Glu|Gly|Pro|Leu|Gly|Gln|Thr|Lys|Phe|
|2465| | | | |2470| | | | |2475| | | | |2480|

Leu Glu Asp Lys Pro Gln Phe Ile Ser Arg Gly Thr Phe Asn Pro Glu
            2485                      2490                      2495

Lys Gly Lys Gln Lys Leu Lys Asn Val Lys Asn Ser Pro Gln Lys Thr
        2500                      2505                      2510

Lys Glu Thr Pro Glu Gly Thr Val Met Ser Gly Arg Arg Lys Thr Val
        2515                      2520                      2525

Asp Pro Asp Cys Thr Ser Asn Gln Gln Leu Ala Leu Phe Gly Asn Asn
            2530                      2535                      2540

Glu Phe Met Val
2545

<210> SEQ ID NO 2
<211> LENGTH: 8473
<212> TYPE: DNA
<213> ORGANISM: Homo sapien

<400> SEQUENCE: 2

```
gcgtccgctc gcccggaccc tgaggctgct gggcccaccc tcccggaacc gtccgaccct      60
cggtggcctc ggctcgttct gccatctccg gtcctaccct ggggcggagg gtggaaggca     120
gcttccgtcg aagaggaggg ggctgcggtg ccaccgcgg cggagcccga gttattttac      180
caagaaaatg gtttgcacga ctttgaacat atactatcca tgctgatggg acaggatcca     240
atatgaatat aaatgatgga ggaagacgac gctttgaaga taatgaacat acattacgga     300
tatatcctgg ggctatttca gagggacaa tctactgtcc gattcctgcc agaaaaaact      360
ccacagctgc tgaggtgatt gagtctctta taaacaaact tcatcttgac aaaacaaaat     420
gttacgttct agcagaggta aaggaatttg gtggagaaga atggattctc aatccaacag     480
attgtccagt tcagcaaatg atgctgtggc cccgaatggc tctggaaaat cgcttaagtg     540
gagaagacta ccgcttcctt ctgagagaga aaaaccttga tggatcaatc cattatggta     600
gcctgcagtc atggctacgg gtaacagaag aacgtcgcag gatgatggaa cggggttttc     660
ttccacagcc tcaacagaaa gactttgatg atttatgtag tttacctgat tgaatgaga       720
aaactctctt agaaacccta cgagatcgct ttaagcatga aaaatttat acctatgttg       780
gcagtattct aatagttatt aacccattca gtttcttcc tatttataac cccaaatatg      840
tcaaaatgta tgataaccac caactgggaa aacctgagcc ccacatttat gctgtggctg     900
atgtagctta tcatgccatg cttcagcgca aaagaatca gtgcatcgtg atttcaggag     960
agagtggttc tgggaagact caaagcacaa actttcttat tcaccacctt actgctctca    1020
gtcagaaagg atttgccagt ggagtagaac agattattct tggagctgga ccagtacttg    1080
aggcctttgg aaatgcaaag acagctcata taacaattc aagtcgtttt gggaagttta    1140
ttcaagtaaa ttaccaggaa acaggcactg tacttggtgc ctatgttgaa aaatatctac    1200
tggagaagtc cagactcgtt tatcaggagc ataatgaacg gaactatcat gtattctatt    1260
acctcctggc aggagcaagt gaagatgaga gatcagcatt ccatcttaag caaccagagg    1320
aatatcatta tctcaatcag ataacaaaga acccctcag acagagctgg gatgattatt      1380
gctatgactc tgagccggat tgcttcacgg tggaaggaga gatttgaga catgactttg      1440
agcgcctaca acttgccatg gaaatggtag gatttcttcc caagacacga agacagattt    1500
tctctcttct ctcagccata ctacatttgg gtaatatctg ttacaaaaag aagacatacc    1560
gggatgactc cattgatatc tgtaatcctg aagttctgcc tattgtctca gaattattag    1620
```

-continued

```
aggttaaaga agagatgcta tttgaagcat tagttacaag gaagacggtg acagtgggag    1680
aaaagcttat tttgccatac aagttggcag aggctgtgac agtgaggaac tccatggcta    1740
agtctctgta tagtgccctg tttgactgga tagttttcg aattaatcat gcacttctga     1800
atagtaaaga tttagagcat aataccaaga cattgtctat tggtgttctt gatattttg     1860 ggtttgaaga ttatgaaaat aacagctttg aacagttctg tattaatttt gctaatgaac    1920
gtttacagca ctactttaat cagcatatct ttaaattgga acaagaggaa tatagaactg    1980
aaggtatcag ctggcacaac atagattaca ttgataatac ctgctgcata aatcttatta    2040
gcaaaaaacc aacaggactg cttcatcttt tggatgaaga agcaacttt ccacaggcta     2100 caaatcaaac attgctagac aagtttaagc atcaacatga agataattct tacatcgaat    2160
ttccagccgt gatggagcct gctttcatta taaacatta tgctggaaaa gtaaaatatg     2220
gggtaaagga tttccgggaa aaaatacag atcatatgcg cccagacatt gtagctcttc     2280
tgagaagcag caagaatgca tttatctctg ggatgattgg aattgatcct gtagctgttt    2340
tccgatgggc aattctccga gcttttttca gagccatggt tgctttcagg aagctggga    2400 aaagaaacat tcacagaaaa actggacatg atgatacagc gccatgtgca attttgaaaa    2460
gtatggatag ttttagcttt ctccaacacc cagtccacca gaggagctta gagattctgc    2520
agagatgcaa ggaagagaag tacagtataa cccggaaaaa tcccagaaca cctctttctg    2580
atctccaggg catgaatgct ctaaatgaaa aaaccaaca tgatacattt gatattgcct     2640
ggaatggcag aactgggatt cgccagagca gactatcaag tggcacctcc ttgcttgata    2700
aagatggaat atttgctaat tcaactagca gcaaactcct ggagagagcc catggaattc    2760
tcacgagaaa caaaaatttc aaatccaagc ctgcccttcc aaagcacttg ctagaagtaa    2820
attcttaaaa gcacctgaca agactgacac tacaagatcg cattaccaag tctcttcttc    2880
atttacacaa gaagaaaaaa cctcccagca tcagtgccca gtttcaggca tcattaagca    2940
agctaatgga aacacttggt caagcagaac catattttgt aaaatgcatt cgctctaatg    3000
ctgaaaagct gcccttaagg ttcagtgatg tcttggtact tagacagctt cgatacaccg    3060
ggatgctgga aacagttcaa attcgccaat caggatacag ctccaaatat tctttccagg    3120
attttgtgag ccacttccat gtacttcttc cccgaaatat tattccatcc aaatttaaca    3180
ttcaggattt cttcaggaaa ataaatctta atccagataa ttatcaagtt ggaaaaacca    3240 tggtcttttct aaaggagcag gaacgacagc acttacaaga tctgcttcac caagaggtgc    3300
tccgcagaat catattgttg cagcgatggt tcagggtctt gctgtgtagg cagcatttcc    3360
tccatctgag acaagcatct gttattatcc agagattctg gaggaattac ctaaatcaga    3420
agcaagtcag agatgcagct gtgcagaagg atgcttttgt tatggctagt gcagctgctc    3480
ttctccaagc ttcctggcgt gctcacttag agaggcagcg gtacttggag ttacgggctg    3540
cagccatcgt tatccagcag aaatggagag attactatag gcgcaggcac atggctgcta    3600
tttgcataca agcaagatgg aaagcctaca gggaaagtaa aagtaccaa gaacaaagga     3660 aaaaaattat ccttttgcaa tcaacatgta gaggattcag agcaagacaa agatttaaag    3720
ctttaaaaga acaaaggcta agagaaacaa agccagaagt tggattggtg aatattaagg    3780
gatatggatc tctggaaatt cagggttcag acccttcaga atgggaggat tgttcttttg    3840
acaacagaat aaaagccata gaggaatgta atctgtaat agagagtaat cgaattagcc    3900
gtgaaagttc agtggactgc ttgaaggagt caccaaacaa gcagcaggag agagcccaaa    3960
```

```
gccagagtgg tgtggacttg caggaagatg tgcttgtaag agagagaccc aggtccttgg    4020
aggatctcca tcagaaaaaa gtaggccggg ctaagagaga agtaggaga atgagagaac     4080 tagagcaagc tatatttagc ttagaattgc tgaaagttcg ttctcttggt ggtatttctc    4140
cttcagagga tcgcagatgg tctacagaat tggtgcctga aggccttcag tctccacggg    4200
gtacacctga tagtgagagc tctcaaggaa gcttggaact tctgagctat gaggaaagcc    4260
aaaagagcaa actagagtct gtcatttcag atgaaggaga cttgcagttt ccatcaccta    4320
agatatccag cagtccaaaa tttgattcac gggacaatgc cctcagtgcc tcaaatgaga    4380
ctagcagtgc agagcatttg aaggatggaa ctatgaagga aatggtggtc tgcagttctg    4440
agtctattac ctgtaaacca cagctgaaag actccttcat ttcaaatagt ctacctactt    4500 tttttttatat cccccaacaa gacccactga aaacaaattc ccaactagac acaagtatcc   4560
aaagaaacaa actattggaa aatgaagaca cagcgggga agctcttact ttggatatca     4620
acagggaaac tagaaggtat cactgctcag gaaaagatca gattgttcct tctttgaata    4680
cagagtcttc taatcctgtg cttaagaagt tagaaaagct aaacactgag aaggaagaaa    4740
ggcaaaaaca gttgcagcaa cagaatgaaa aagagatgat ggaacagatt cgccagcaaa    4800
cagatatttt agagaaggag cgcaaagcct tcaagacaat tgaaaagcca agaattggag    4860
agtgtttggt ggcaccatct tcctatcagt caaagcaaag agtagagagg ccatcctctc    4920
tcctcagctt aaatacctca ataagggag aacttaatgt actggggtcc ctatcattaa     4980
aagatgcagc tcttgcccaa aaagacagtt cctctgctca cttacccca aaggaccgac     5040 ctgtcaccgt gttctttgaa agaaaaggaa gtccatgcca atctagtact gtcaaggaat    5100
tatccaagac agacagaatg ggcacccagc tgaatgtagc ctgtaaactc tcaaataatc    5160
gcatttcaaa aagagaacac tttaggccaa ctcagtctta cagccacaat tctgatgacc    5220
tttccagaga gggaaatgct aggcccattt tcttcactcc aaaggataat atgagtattc    5280
cccttgtcag caaagaagcc ttaaacagta aaatcctca actccataaa gaagatgaac     5340
cagcatggaa acctgtgaag ttagctgggc caggccaaag agagacatca cagcgatttt    5400
cgtcagttga tgaacaagca aaacttcata agactatgtc tcaaggagag attaccaagt    5460
tggcagtgag acagaaggct tcagattcag atataagacc tcagagagct aagatgagat    5520
tctgggccaa agggaaacaa ggggagaaga agactaccag agtgaaacct actcccagt     5580 cagaggtttc gccactcttt gcaggcacag atgtgattcc agctcatcag tttccagatg    5640
aattagctgc atatcaccca acacctcctt tgagcccaga actgcccggc agttgccgga    5700
aggaattcaa agagaacaaa gaaccttctc caaaggctaa gcgcaagcga agtgtgaaga    5760
ttagcaacgt ggctttggat tctatgcatt ggcaaaatga ctctgtccag atcatagcaa    5820
gtgtcagtga tttaaaaagc atggatgaat tccttctgaa aaaggtgaat gacctagata    5880
atgaagacag caagaaggat acactagtgg atgttgtatt taaaaaagcc ctgaaggaat    5940
ttcggcagaa tatcttcagc ttttattcat ctgcattggc gatggatgat gggaaaagca    6000
tacggtataa agacctctat gcactatttg aacagattct ggaaaagacg atgaggcttg    6060
agcagcgtga ttcactgggt gaatctccag tgagagtttg ggtcaacact tttaaagtgt    6120
ttttagatga atatatgaat gaattcaaga cttcagattg cacagccaca aaggtgccaa    6180
aaacagaaag aaagaaaaga aggaaaaagg aaactgattt ggtggaagaa cacaatggtc    6240
acatctttaa agccacccaa tatagcatcc ctacatactg tgaatactgt tcttctttga    6300
tatggataat ggaccgagcc tctgtttgca aattatgcaa gtatgcttgc cataagaagt    6360
```

```
gctgtctgaa aaccacagcc aagtgctcta aaaagtatga tccagagctg tcatctcgac    6420
aatttggggt tgaactgtcc cgtttgacca gtgaagaccg aactgttcct ttagtagtgg    6480
aaaagctcat aaactacatt gaaatgcatg gactgtatac agaaggtatt tatcgaaagt    6540
ctggttcgac taataaaatc aaggagcttc ggcagggtct agatacagat gctgagagtg    6600
taaatctaga tgactataac atacacgtca ttgcaagtgt attcaaacaa tggcttcgag    6660
atttgcccaa tcctctcatg acctttgaac tctatgagga atttcttcga gctatgggcc    6720
ttcaggagag gaaggagaca atccgtggtg tatactctgt gattgatcaa ctctcccgaa    6780
ctcatctcaa tacactggaa cgcctcatct ttcatctagt caggattgct ctgcaggaag    6840
acactaatcg aatgtctgct aatgctttgg ccattgtgtt tgcgccctgc attctccgct    6900
gccctgacac cactgaccca ctacaaagtg tacaggacat cagtaagact accacttgtg    6960
tggaactgat tgttgtggaa caaatgaata aatacaaggc tcgtctcaaa gatatcagta    7020
gcttggaatt tgctgagaat aaggcaaaga ccaggttgtc actgattcgt agatcaatgg    7080 gaaagggggcg tattcgtcga ggaaactatc caggtccatc gtctcctgtt gtagttcggt    7140
tgccttctgt gtctgatgtc tcagaggaga ccttgactag tgaggcagcc atggagactg    7200
acatcacaga acagcagcaa gcagctatgc agcaggagga gagtactg actgagcaga    7260 ttgagaacct acagaaggag aaggaggagc taacatttga gatgcttgta ctggaacccc    7320
gtgcctctga tgatgaaacc cttgagtctg aggcctccat tgggactgct gatagctcag    7380
agaatttgaa tatggagtct gaatatgcta tctctgagaa atcagaaaga agcttagccc    7440
ttagctccct gaagacagct ggcaagtctg aaccttccag caagttgcga aagcaactta    7500
aaaagcagca agactctttta gatgtcgtgg actcttcggt ctcctcttta tgtctgtcta    7560
acacggcatc atctcatggg accagaaaac tatttcagat ttattccaaa tctccattct    7620
accgagctgc ctcaggtaat gaggccctgg gaatggaagg accattgggc cagaccaaat    7680
tcctggaaga caagcctcag ttcatcagca gaggaacctt caacccggaa aagggcaaac    7740
aaaaattaaa gaatgtgaaa aactcacctc agaaaaccaa agagacccca gagggggacag    7800 tcatgtctgg ccgcagaaaa actgtggacc cagactgcac ctccaaccaa cagctagcac    7860
tctttggaaa taatgaattt atggtctgaa ccggcagatg tgtgtccctc cgtggctaca    7920
gagtggtaaa caaatctcac ctttggggct gcgtttcatc acctcgtcca caatagtcaa    7980
tcctaattgt ggtcctgcct cttttctaag catatggcta agactgtatg tgctgaattc    8040
ctgggcctcc tgcagaagca gaaagcctgc tggggatggt gccagctgtg ccttggctgt    8100
tgtatttgaa ttgagatttt tactatacaa agccacctag ggcctgggga tttgggtcag    8160
ttgtagttgc ctctccccca ccctcttttc ccttcccaaa ggtgggtgtt gaactagggg    8220
ggatattgct gtcctgaggg accctctcat ttctgacatt tgaagaaaac gtataaatct    8280
ttcttaaccg tgaaagcaaa agcctttggg tttattttgg gatagttagg agctagggta    8340
gaatataatt tttttccaaa aacttactta caaacaaaaa gcctaatccc tctattttaa    8400
gatttctgaa aaaacactcc atgttatatt ctggggaaag caaaaacaaa aaaaaaaaa    8460 aaaaaaaaa aaa                                                         8473
```

<210> SEQ ID NO 3
<211> LENGTH: 1307
<212> TYPE: DNA
<213> ORGANISM: Homo sapien
<220> FEATURE:

-continued

```
<221> NAME/KEY: misc_feature
<222> LOCATION: (1)...(1307)
<223> OTHER INFORMATION: n = A,T,C or G

<400> SEQUENCE: 3
gaattcgggc ttccatcctt aataggaact caatnntagg gctngggcgg ccgcccgggc      60
aggtgcgcga acaggagagg gtcaagtcgg ccggattttg gattatccac ccctacagtg     120
acttcagatt ttactgggac ctgaccatgc tgctgctgat ggtgggaaac ctgattatca    180
ttcctgtggg catcaccttc ttcaaggatg agaacaccac accctggatt gtcttcaatg    240
tggtgtcaga cacattcttc ctcatcgact tggtcttcaa cttccgcaca gggatcgtgg    300
tggaggacaa cacagagatc atcctggacc cgcagcggat taaaatgaag tacctgaaaa    360
gctggttcat ggtagatttc atttcctcca tcccccgtgg aaaacatctt cctcattgtg    420
gagacaggca tcgactcgga ggtctacaag actgcccggg ccctgcgcat tgtccgcttc    480
acgaagatcc tcagcctctt acgcctgtta cgcctctccc gcctcattcg atatattcac    540
cagtgggaag agatcttcca catgacctac gacctggcca gcgccgtggt gcgcatcgtg    600
aacctcatcg gcatgatgct cctgctctgc cactgggacg gctgcctgca gttcctggta    660
cccatgctac aggacttccc tgacgactgc tgggtgtcca tcaacaacat ggtgaacaac    720
tcctggggga agcagtactc ctacgcgctc ttcaaggcca tgagccacat gctgtgcatc    780
ggctacgggc ggcaggcgcc cgtgggcatc tccgacgtct ggctcaccat gctcagcatg    840
atcgtgggtg ccacctgcta cgccatgttc attggccacg ccactgccct catccagtcc    900
ctggactcct cccggcgcca gtaccaggaa aagtacaagc aggtggagca gtacatgtcc    960
tttcacaagc tcccgcccga cacccggcag cgcatccacg actactacga gcaccgctac   1020
cagggcaaga tgttcgacga ggagagcacc ctgggcgagc taagcgagcc cctgcgggag   1080
gagatcatca actttaactg tcggaagctg gtggcctcca tgccactgtt tgccaatgcg   1140
gaccccaact tcgtgacgtc catgctgacc aagctgcgtt tcgaggtctt ccagcctggg   1200
gactacatca tccgggaagg caccattggc aagaagatgt acttcatcca gcatggcgtg   1260
gtcagcgtgc tcaccaaggg caacaaggag accaagaagc cgaattc                 1307
```